US006991927B2

(12) United States Patent
Mross et al.

(10) Patent No.: US 6,991,927 B2
(45) Date of Patent: Jan. 31, 2006

(54) APPLYING FAR INFRARED RADIATION TO BIOLOGICAL MATTER

(75) Inventors: Michael R. Mross, Putney, VT (US); Thomas H. Lowell, Dummerston, VT (US); Robert Durant, Dummerston, VT (US); Nigel Dyer, Coventry (GB); Lila M. Gierasch, Amherst, MA (US); Gerald H. Pollack, Seattle, WA (US)

(73) Assignee: Vermont Photonics Technologies Corp., Bellows Falls, VT (US)

( * ) Notice: Subject to any disclaimer, the term of this patent is extended or adjusted under 35 U.S.C. 154(b) by 74 days.

(21) Appl. No.: 10/104,980

(22) Filed: Mar. 22, 2002

(65) Prior Publication Data

US 2002/0187533 A1 Dec. 12, 2002

Related U.S. Application Data

(60) Provisional application No. 60/278,359, filed on Mar. 23, 2001.

(51) Int. Cl.
*C12N 13/00* (2006.01)
*G01D 5/30* (2006.01)
*G21F 5/02* (2006.01)

(52) U.S. Cl. ............... 435/173.1; 250/330; 250/496.1; 250/504 R

(58) Field of Classification Search ............ 435/173.1, 435/173.2; 250/338.1, 330, 331, 332, 333, 250/334, 335, 505.1, 504 R, 503.1, 498.1, 250/496.1, 497.1
See application file for complete search history.

(56) References Cited

U.S. PATENT DOCUMENTS

| | | | |
|---|---|---|---|
| 3,639,774 A | 2/1972 | Wolff | 307/88.3 |
| 3,958,189 A | 5/1976 | Sprangle et al. | 331/94.5 PE |
| 4,215,320 A | 7/1980 | Chang | 331/94.5 G |
| 4,255,017 A | 3/1981 | Hasegawa | 350/96.29 |
| 4,438,513 A | 3/1984 | Elias et al. | 372/2 |
| 4,491,948 A | 1/1985 | Deacon et al. | 372/2 |
| 4,529,942 A | 7/1985 | Patel et al. | 330/4.3 |
| 4,538,275 A | 8/1985 | Szu | 372/4 |
| 4,663,932 A | 5/1987 | Cox | 60/200.1 |
| 4,682,053 A | 7/1987 | Pickett et al. | 307/425 |
| 4,727,550 A | 2/1988 | Chang et al. | 372/2 |
| 4,740,973 A | 4/1988 | Madey et al. | 372/2 |
| 4,874,953 A | 10/1989 | Katz | 250/493.1 |
| 4,891,600 A | 1/1990 | Cox | 328/233 |
| 5,060,232 A | 10/1991 | Etievant | 372/2 |
| 5,243,618 A | 9/1993 | Dolezal et al. | 372/92 |
| 5,263,043 A | 11/1993 | Walsh | 372/102 |
| 5,268,693 A | 12/1993 | Walsh | 372/74 |
| 5,736,709 A | 4/1998 | Neiheisel | 219/121.61 |
| 5,790,585 A | 8/1998 | Walsh | 372/102 |
| 5,948,172 A | 9/1999 | Neiheisel | 134/1 |
| 6,060,293 A | 5/2000 | Bohr et al. | 435/173.1 |
| 6,196,226 B1 | 3/2001 | Hochman et al. | 128/653.1 |
| 2002/0097755 A1 | 7/2002 | Mross et al. | 372/9 |

FOREIGN PATENT DOCUMENTS

DE WO 00/72413 A2 5/2000

OTHER PUBLICATIONS

Maurice F. Kimmitt, "Far Infrared Techniques" (1970) Pion Limited, London, pp. 2-43.*
Qiong Wang, Robert W. Schoenlein, Linda A. Peteanu, Richard A. Mathies, Charles V. Shank, (1994), "Vibrationally Coherent Photochemistry in the Femtosecond Primary Event of Vision", *Science* vol. 226: pp. 422-424.
Leyun Zhu, J. Timothy Sage, Paul M. Champion, (1994), "Observation of Coherent Reaction Dynamics in Heme Proteins", *Science*, pp. 629-631.
Diehl M, Doster W, Petry W, Schober H, (1997), "Water-coupled low-frequency modes of myoglobin and lysozyme observed by inelastic neutron scattering", *Biophys Journal* vol. 73(5), pp. 2726-2732.
Aihua Zie, Alexander F.G. van der Meer, Robert H. Austin, (2001). "Excited-State Lifetimes of Far-Infrared Collective Modes in Proteins", *Physical Review Letters* vol. 88 (1), pp. 018102-1-018102-4.
Joel E. Boyd, Ari Briskman, and Vicki L. Colvin, (2001) "Direct Observation of Terahertz Surface Modes in Nanometer-Sized Liquid Water Pools", *Physical Review Letters*, vol. 87 (14), pp. 147401-1-147401-4.
Yufeng Zhou, Joao H. Morais-Cabral, Amelia Kaufman & Roderick MacKinnon, (2001), "Chemistry in ion coordination and hydration revealed by a K+ channel-Fab complx at 2.0 A resolution", *Nature* vol. 144, pp. 43-48.
Donald E. Ingber, (1998) "The Architecture of Life", *Scientific American*, vol. 278(1): Cover Story.
J, Hone, B. Batlogg, Z. Benes, A.T. Johnson, J.E. Fischer, (Sep.), "Quantized Phonon Spectrum of Single-Wall Carbon Nanotubes", *Science*, pp. 1730-1733.

(Continued)

*Primary Examiner*—Jean C. Witz
*Assistant Examiner*—Susan Hanley
(74) *Attorney, Agent, or Firm*—Scott E. Kamholz; Foley Hoag LLP

(57) ABSTRACT

A method is disclosed for irradiating a biological sample with far infrared (FIR) irradiation, including providing tunable FIR irradiation, removing X rays from the irradiation, and irradiating at least one biological sample with the tunable FIR irradiation, wherein at least a component of the biological sample undergoes at least one of a conformational change or a phase change in response to the irradiating. An FIR irradiation device is disclosed, including an FIR source producing an FIR irradiation having a tunable wavelength, the source being capable of continuous-wave output, and a filter receiving the irradiation from the source.

69 Claims, 7 Drawing Sheets

OTHER PUBLICATIONS

R. Savage, *"What are microtubules?"*, pp. 1-3 [retrieved on Jan. 10, 2001]. Retrieved from the Internet: <URL:www.reed.edu/~rsavage/microtubules.html>.

Department of Physics, Tuszynski Group, Microtubules, (Jan.) *"Physical Properties of Microtubules"*, pp. 1-3 [retrieved on Jan. 10, 2001]. Retrieved from the Internet: <URL: www.phys.ualberta.ca/~biophys/microtubules.html>.

Hans Frauenfelder, Stephen G. Sligar, Peter G. Wolynes, (1991), "The Energy Landscapes and Motions of Proteins", *Science* vol. 254, pp. 1598-1603.

Robert H. Austin, Mark W. Roberson, and Paul Mansky, (1988), "Far-Infrared Perturbation of Reaction Rates in Myoglobin at Low Temperatures", *Physical Review Letters* vol. 62 (16), pp. 1912-1915.

Carlo Sirtori, (2002) "Bridge for the Terahertz Gap", *Nature* vol. 417, pp. 132-133.

Rüdeger Köhler, Alessandro Tredicucci, Fabio Beltram, Harvey E. Beere, Edmund H. Linfield, A. Giles Davies, David A. Ritchie, Rita C. Iotti & Fausto Rossi, (2002) "Terahertz semiconductor-heterostructure laser", *Nature*, pp. 156-159.

Minute of the Bordeaux Forum, (2000), "Future European Research on Mobile Communication and Health", pp. 1-3 [retrieved on Feb. 21, 2002]. Retrieved from the Internet: <URL: www.frascati.enea.it/THz-BRIDGE/Bordeaux99.htm>.

J.E. Walsh, J.H. Brownell, J.C. Swartz, (1999), "A New Source of THz-FIR Radiation", pp. 1-9 [retrieved on Jun. 11, 2001]. Retrieved from the Internet: <URL: ieee.org/organizations/pubs/newsletters/leos/feb99/hot2.htm>.

The University of Chicago Department of Physics, (2001), "Research", pp. 1-4 [retrieved on Feb. 11, 2002]. Retrieved from the Internet: <URL: physics.uchicage.edu/research.html>.

E. Schamioglu, S.R.J. Brueck, and F. Hegeler, *"A Smith-Purcell Free Electron Laser Based On An X-Band Photoinjector"*, pp. 1-2 [retrieved on Oct. 11, 2002]. Retrieved from the Internet <URL: tempest.das.ucdavis.edu/muri95/icops/5b04.pdf>.

Division of Infrared Spectroscopy, "Research Field", pp. 1-4 [retrieved on Feb. 11, 2002]. Retrieved from the Internet: <URL: www.rism.tohoku.ac.jp/irlab/topics.html>.

(1999), "Characterization of Biological Systems with Far Infrared and THz Radiation", pp. 1-3 [retrieved on Feb. 21, 2002]. Retrieved from the Internet: <URL; www.frascati.enea.it/THz-BRIDGE/May3summary.htm>.

(2001), "TH-zBrdige progress report", pp. 1-6 [retrieved on Oct. 11, 2002]. Retrieved from the Internet: <URL: www.frascati.enea.it/THz-BRIDGE/progress_reports/THz-BRIDGE%20prog%20rep.doc>.

(2001), "THz-Bridge Progress Report", pp. 1-7 [retrieved on Oct. 11, 2002]. Retrieved from the Internet: <URL: www.frascati.enea.it/THz-BRIDGE/progress_reports/9-month-reports.PDF>.

THz-Bridge, "Objectives and Expected Achievements"pp. 1-6 [retrieved on Feb. 11, 2002]. Retrieved from the Internet: <URL: www.frascati.enea.it/THz-BRIDGE/descr_gen2.htm>.

Hayward S, Kitao A, Berendsen HJ, (1997), "Model-free methods of analylzing domain motions in proteins from simulation: a comparison of normal mode analysis and molecular dynamics simulation of lysozyme", *PubMed* vol. 27 (3), p. 1.

M.F. Kimmitt, (1970), *Far-Infrared Techniques*, Pion Limited, pp. 12-43.

English Translation of WO 00/72413A2, May 10, 2000, Elsässer et al.

J. Urata, M. Goldstein, M.F. Kimmitt, A. Naumov, C. Platt, and J.E. Walsh, (1998) "Superradiant Smith-Purcell Emission", *Physical Review Letters* vol. 80(3), pp. 516-519.

D.L. Woolard, T.R. Globus, B.L. Gelmont, M. Bykhovskaia, A.C. Sameuls, D. Cookmeyer, J.L. Hesler, T.W. Crowe, J.O. Jensen, J.L. Jensen, and W.R. Leorop, (2002) "Submillimeter-wave Phonon Modes in DNA Macromolecules", *Physical Review E* vol. 65 pp. 051903-1-051903-11.

"THz-Bridge Progress Report" (period from Feb. 1 to Jul. 31, 2002), pp. 1-13 [retrieved on Oct. 11, 2002]. Retrieved from the Internet: <URL: www.frascati.enea.it/THz-BRIDGE/progress_reports/16-month-report.PDF>.

International Search Report, PCT Pub. No. WO 02/077607, filed Oct. 3, 2002.

* cited by examiner

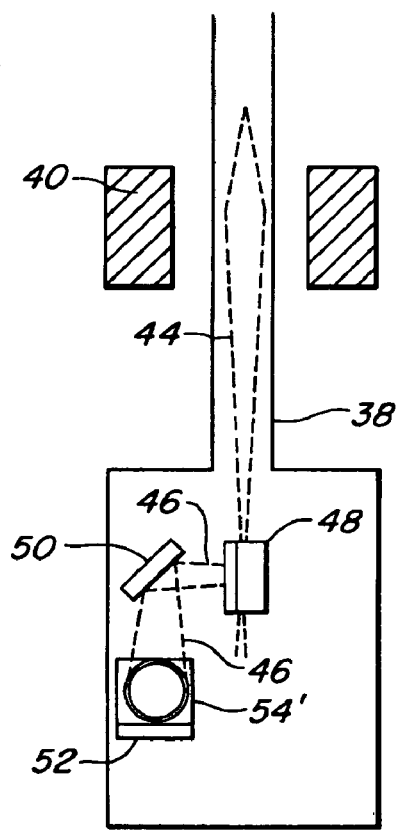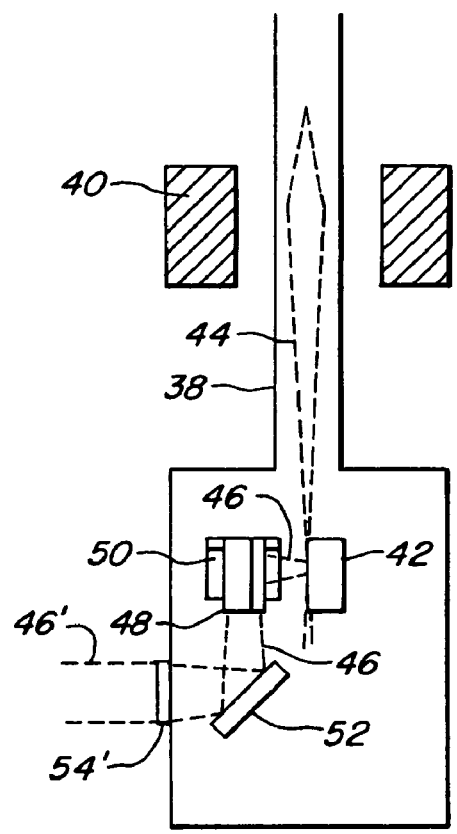
*FIG. 5A*  *FIG. 5B*

APPLYING FAR INFRARED RADIATION TO BIOLOGICAL MATTER

CROSS-REFERENCE TO RELATED APPLICATION

This application claims the benefit of priority of U.S. Provisional Application Ser. No. 60/278,359, filed Mar. 23, 2001, which is incorporated in its entirety by this reference.

BACKGROUND

The disclosed devices, apparatuses, methods, assays, and processes relate generally to applying radiant electromagnetic energy to biological material, and, more particularly, relate to the application of radiant electromagnetic energy in the far-infrared (FIR) region of the electromagnetic spectrum to biological material with minimal contamination by radiation in other electromagnetic bands (such as X-rays and microwaves).

The term "far infrared" (FIR) identifies the range of the electromagnetic spectrum with free space wavelengths of about 100 to 1000 microns, or with wavenumbers from about 100 to 10 $cm^{-1}$. Humans have developed extensive technology to generate and detect electromagnetic waves or vibrations throughout the electromagnetic spectrum—from the very short wavelengths and very high frequencies of gamma rays to the very long wavelengths and very low frequencies of radio waves—with the exception of the FIR gap in the spectrum existing between infrared light and millimeter wavelength microwaves. For use in the FIR gap there exists various sources and detectors, but this technology is much less well developed than the technology available for use in the other parts of the spectrum.

In the late 1980's, the research of the late Professor John Walsh at Dartmouth College and others led to the development of tunable, electron beam driven radiation sources to produce electromagnetic radiation at FIR frequencies in a flexible, tunable and affordable fashion. See U.S. Pat. No. 5,263,043 to Walsh and U.S. Pat. No. 5,790,585 to Walsh, both of which are incorporated in their entireties by this reference. This work showed that a small, compact and relatively inexpensive table top free electron laser could be a commercially practiced device to generate FIR electromagnetic waves.

Previously in the art, the common wisdom was that large biomolecules could not support vibrations, especially considering that they were always in water. Physicists thought that any possible mode of vibration would be seriously overdamped. That is to say, proteins were seen (from a mechanical point of view) more as sponges that would just go "thunk" if struck (i.e., exposed to mechanical perturbation or electromagnetic radiant energy), rather than as bells or springs which would ring or vibrate when struck. In the terminology of classical physics, it was believed that a protein structure, while having restoring forces which tend to pull the structure back towards its equilibrium conformation when the structure is forced away from its equilibrium conformation or physical shape by external forces of any nature, would not oscillate about its equilibrium conformation because the damping forces inherent in the structure and its environment would be sufficiently strong to preclude any oscillation.

However, several practitioners in the art have reported evidence that proteins are capable of vibration, even in aqueous environments. Furthermore, a number of practitioners have reported that certain proteins vibrate in the FIR band. In 1994, it was reported that the first event following impact of a visible photon on the retinal chromophore of rhodopsin was the initiation of a vibration at wavenumber 60 $cm^{-1}$ (corresponding to a far infrared wavelength of about 166 microns) (Wang Q et al, "Vibrationally coherent photochemistry in the femtosecond primary event of vision," Science, Vol. 266, 21 October 1994, p. 422). Also in 1994, researchers reported that "breathing modes" of myoglobin oscillate at FIR frequencies in association with ligand binding (binding of the oxygen which is transported by myoglobin) and that the vibrations are not overdamped (Zhu L et al, "Observation of coherent reaction dynamics in heme proteins," Science, Vol. 266, 21 October 1994, p.629). Other experimentalists observed low frequency modes (near 20 $cm^{-1}$) (Diehl M et al, "Water-coupled low-frequency modes of myoglobin and lysozyme observed by inelastic neutron scattering," Biophysical Journal, 1997 November; 73(5): 2726–32). Such results have generated further interest in the existence of vibrational modes in proteins, and, more particularly, vibrational modes in the FIR frequency range. Other recent work reinforces earlier findings that proteins and water can have modes in the FIR range (Xie A et al., Phys. Rev. Ltr. (2002) 88:1, 018102-1; Boyd JE et al., Phys. Rev. Ltr. (2001) 84:14, 147401-1). There are also suggestions that water associated with the KcsA potassium channel may be structured (Zhou Y et al., Nature (2001) 414:43–48).

However, no practical means exists in the art to produce and apply electromagnetic energy selectively from the FIR band to biological matter (i.e., with minimal contamination by energy from other bands, such as X-rays and microwaves). Bohr et al, in U.S. Pat. No. 6,060,293, the entire disclosure of which is incorporated herein by reference, teach methods of application of Gigahertz frequency radiation to biological matter. However, delivery of FIR radiation to biological matter requires methods and apparatus for the generation, filtering, and focusing of the FIR radiation clearly distinct from those taught by Bohr et al.

The instantly disclosed subject matter enhances the art by providing devices, apparatuses, methods, assays, and processes for delivering FIR band radiation with minimal contamination by energy in other electromagnetic bands to biological matter.

SUMMARY

In a first embodiment, a method of irradiating a biological sample with far infrared (FIR) irradiation includes providing tunable FIR irradiation, removing X rays from the irradiation, and irradiating at least one biological sample with the tunable FIR irradiation, wherein at least a component of the biological sample undergoes at least one of a conformational change or a phase change in response to the irradiating.

In a second embodiment, an assay includes providing tunable FIR irradiation, removing X rays from the irradiation, irradiating at least one biological sample with the tunable FIR irradiation, providing compounds, allowing the biological sample to bind to at least one compound, and measuring a binding affinity between the at least one biological sample and the at least one compound. In a related embodiment, the irradiating disrupts an interaction between the biological sample and the at least one compound.

In a third embodiment, a method of detecting an impurity in an article includes providing FIR irradiation having a characteristic that is selective for the impurity, removing X rays from the irradiation, irradiating at least a component of the article with the irradiation, and detecting a residual irradiation emitted from at least the component of the article.

In a fourth embodiment, a diagnostic method includes providing tunable FIR irradiation, removing X rays from the irradiation, irradiating at least a component of a biological sample with the irradiation, and detecting a residual irradiation emitted from at least the component of the biological sample.

In a fifth embodiment, a free-electron laser process for generating coherent stimulated electromagnetic radiation includes passing a beam of electrons along a path extending over a diffraction grating element to produce interaction electromagnetic radiation, at least a first mode of the interaction electromagnetic radiation being directed along a selected axis substantially parallel to the path of the beam, providing feedback of at least the first mode of the interaction electromagnetic radiation, controlling the current of the beam of electrons for selectively increasing the current at least up to a feedback beam current level to provide feedback from a resonator element of at least the first mode of the interaction electromagnetic radiation for achieving the stimulated radiation, and removing X rays from the stimulated radiation.

In a sixth embodiment, a far infrared (FIR) irradiation device includes an FIR source producing an FIR irradiation having a tunable wavelength, the source being capable of continuous-wave output, and a filter receiving the irradiation from the source.

In a seventh embodiment, a laser apparatus for generating coherent electromagnetic laser radiation includes resonator means for defining a resonant cavity in which stimulated radiation can propagate to generate coherent electromagnetic laser radiation, the resonator means including at least a first diffraction grating means for defining a geometrically periodic coupling structure, means for directing a beam of electrons over the diffraction grating means to excite an electromagnetic field through which the electron beam propagates, the beam of electrons having a beam thickness selected relative to the wavelength of the coherent electromagnetic laser radiation, the grating means and the beam directing means being adapted to produce interaction between the beam and the electromagnetic field for generating stimulated radiation, so that the stimulated radiation propagates in the resonant cavity to generate coherent electromagnetic laser radiation, and filter means for removing X rays from the stimulated radiation.

In an eighth embodiment, a free-electron laser apparatus for generating coherent stimulated electromagnetic radiation includes a source of a beam of electrons, diffraction grating means, means for directing a beam of electrons along a path extending over the grating means so that the beam interacts with the grating to produce interaction electromagnetic radiation, at least a first mode of the interaction electromagnetic radiation being directed along a selected axis substantially parallel to the path of the beam, resonator means for providing feedback of at least the first mode of the interaction electromagnetic radiation, means for controlling the current of the beam of electrons for selectively increasing the current at least up to a feedback beam current level to provide feedback from the resonator means of at least the first mode of the interaction electromagnetic radiation for achieving the stimulated radiation, and filter means for removing X rays from the stimulated radiation.

For any of the foregoing embodiments, in an additional embodiment, the biological sample is in a sample cell.

For any of the foregoing embodiments, in an additional embodiment, the sample cell is selected from the group consisting of polymethylpentene, polyester, polypropylene, polyethylene, single crystal quartz, or sapphire, styrene, or any combination thereof.

For any of the foregoing embodiments, in an additional embodiment, the biological sample is suspended in at least one of an aqueous solution or an aqueous gel within the sample cell.

For any of the foregoing embodiments, the biological samples, compounds, or components thereof may be provided in a library. The biological samples, compounds, or components thereof may be disposed on a microarray. The biological samples, compounds, or components thereof may include nucleic acid and/or protein.

In any of the foregoing embodiments, an additional embodiment further includes subjecting the biological sample to an assay.

In any of the foregoing embodiments, an additional embodiment further includes determining at least one of a power of the irradiation, a wavelength of the irradiation, a duration of the irradiation, a pulse rate of the irradiation, a pulse shape of the irradiation, a duty cycle of the irradiation, or a bandwidth of the irradiation at least in part in response to feedback from the assay.

In any of the foregoing embodiments, an additional embodiment further includes receiving a residual quantity of the irradiation by a detector.

In any of the foregoing embodiments, an additional embodiment further includes setting a characteristic of the irradiation at least in part in response to feedback from the detector.

For any of the foregoing embodiments, in an additional embodiment, the characteristic of the irradiation is selected from the group consisting of a power of the irradiation, a wavelength of the irradiation, a duration of the irradiation, a pulse rate of the irradiation, a pulse shape of the irradiation, a duty cycle of the irradiation, or a bandwidth of the irradiation, or any combination thereof.

In any of the foregoing embodiments, an additional embodiment further includes receiving spectroscopic data from the detector in response to the residual quantity of the irradiation.

In any of the foregoing embodiments, an additional embodiment further includes receiving image data from the detector in response to the residual quantity of the irradiation.

In any of the foregoing embodiments, an additional embodiment further includes directing a portion of the irradiation to a detector.

In any of the foregoing embodiments, an additional embodiment further includes determining a characteristic of the irradiation at least in part in response to feedback from the detector.

For any of the foregoing embodiments, in an additional embodiment, the characteristic of the irradiation is selected from the group consisting of a power of the irradiation, a wavelength of the irradiation, a duration of the irradiation, a pulse rate of the irradiation, a pulse shape of the irradiation, a duty cycle of the irradiation, or a bandwidth of the irradiation, or any combination thereof.

In any of the foregoing embodiments, an additional embodiment further includes receiving spectroscopic data in response to the portion of the irradiation.

In any of the foregoing embodiments, an additional embodiment further includes receiving image data from the detector in response to the portion of the irradiation.

For any of the foregoing embodiments, in an additional embodiment, the source is capable of emitting continuous-wave irradiation.

For any of the foregoing embodiments, in an additional embodiment, the irradiation has continuously tunable power.

For any of the foregoing embodiments, in an additional embodiment, the irradiation has continuously tunable wavelength.

For any of the foregoing embodiments, in an additional embodiment, the irradiation has continuously tunable bandwidth.

For any of the foregoing embodiments, in an additional embodiment, the irradiation has continuously tunable pulse rate.

For any of the foregoing embodiments, in an additional embodiment, the irradiation has continuously tunable pulse shape.

For any of the foregoing embodiments, in an additional embodiment, the irradiation has continuously tunable duty cycle.

For any of the foregoing embodiments, in an additional embodiment, the irradiation has a power in the range of about 1 milliwatt per square centimeter to about 1000 milliwatts per square centimeter.

For any of the foregoing embodiments, in an additional embodiment, the irradiation has a power of about 100 milliWatts per square centimeter.

For any of the foregoing embodiments, in an additional embodiment, the irradiation has a power in the range of about 1 picoWatt to about 1 Watt.

For any of the foregoing embodiments, in an additional embodiment, the irradiation has a power in the range of about 0.1 microWatts to about 10 milliwatts.

For any of the foregoing embodiments, in an additional embodiment, the irradiation has a wavelength in the range of about 10 microns to about 3,000 microns.

For any of the foregoing embodiments, in an additional embodiment, the irradiation has a wavelength in the range of about 60 microns to about 1,000 microns.

For any of the foregoing embodiments, in an additional embodiment, the irradiation has a wavelength in the range of about 100 microns to about 500 microns.

For any of the foregoing embodiments, in an additional embodiment, the irradiation has a wavelength in range of about 430 microns to about 480 microns.

For any of the foregoing embodiments, in an additional embodiment, the irradiation has a duration in the range of about 1 microsecond to about 1 hour.

For any of the foregoing embodiments, in an additional embodiment, the irradiation has a duration in the range of about 100 microseconds to about 1 second.

For any of the foregoing embodiments, in an additional embodiment, the irradiation has a duration in the range of about 1 second to about 1 minute.

For any of the foregoing embodiments, in an additional embodiment, the irradiation has a duration in the range of about 1 minute to about 10 minutes.

For any of the foregoing embodiments, in an additional embodiment, the irradiation has a duration of about 3 minutes.

For any of the foregoing embodiments, in an additional embodiment, the irradiation has a bandwidth equal to approximately 0.03 times a center wavenumber of the irradiation.

For any of the foregoing embodiments, in an additional embodiment, the irradiation has a bandwidth in the range of about 0.01 cm$^{-1}$ to about 100 cm$^{-1}$.

For any of the foregoing embodiments, in an additional embodiment, the irradiation has a bandwidth in the range of about 0.01 cm$^{-1}$ to about 1 cm$^{-1}$.

For any of the foregoing embodiments, in an additional embodiment, the irradiation has a bandwidth in the range of about 0.6 cm$^{-1}$.

For any of the foregoing embodiments, in an additional embodiment, the irradiation has a bandwidth in the range of about 1 cm$^{-1}$ to about 100 cm$^{-1}$.

For any of the foregoing embodiments, in an additional embodiment, the irradiation has a pulse rate in the range from continuous wave to about 1 GigaHertz.

For any of the foregoing embodiments, in an additional embodiment, the irradiation has a pulse rate in the range from about 25 Hz to about 55 Hz.

For any of the foregoing embodiments, in an additional embodiment, the irradiation has a duty cycle in the range of about 5 per cent to about 100 per cent.

For any of the foregoing embodiments, in an additional embodiment, the irradiation has a pulse shape comprising at least one of rectangular, triangular, sawtooth, sinusoidal, rectified, or constant.

In any of the foregoing embodiments, an additional embodiment further includes tuning the irradiation to couple selectively with the component of the biological sample.

For any of the foregoing embodiments, in an additional embodiment, the component comprises an organelle.

For any of the foregoing embodiments, in an additional embodiment, the organelle is selected from the group consisting of a nucleus, a cytoskeleton, a centriole, an endoplasmic reticulum, a golgi apparatus, a mitochondrion, a chloroplast, a cell membrane, a nuclear membrane, a cell wall, a lysosome, a vacuole, a vesicle, a ribosome, or a peroxisome, or any combination thereof.

For any of the foregoing embodiments, in an additional embodiment, the component is selected from the group consisting of a mitotic spindle, a DNA polymerase complex, a transcription complex, a protein replication complex, a gene, or a centromere, or any combination thereof.

For any of the foregoing embodiments, in an additional embodiment, the gene is selected from the group consisting of an immunoglobulin gene, a T cell receptor gene, a p53 gene, a retinoblastoma gene, or a proto-oncogene, or any combination thereof.

For any of the foregoing embodiments, in an additional embodiment, the component is selected from the group consisting of a cytoskeleton, a centriole, a nuclear lamin, an intermediate filament, a neurofilament, a nucleic acid, a lipid, a fatty acid, a triglyceride, a phospholipid, a steroid, a polyisoprenoid, a glycolipid, a peptide, a polypeptide, an amino acid, an amino acid-coupled transfer RNA, a nucleotide, a nucleoside, a protein, a heat-shock protein, a histone, an enzyme, a lipoprotein, a monosaccharide, a disaccharide, a polysaccharide, a lipopolysaccharide, a proteoglycan, a glycoprotein, a water molecule, a water cluster, a region of gelled vicinal water, actin, myosin, titin, troponin, tropomyosin, a microtubule, or a microfilament, or any combination thereof.

For any of the foregoing embodiments, in an additional embodiment, the biological sample is an organism.

For any of the foregoing embodiments, in an additional embodiment, the organism is a microorganism.

For any of the foregoing embodiments, in an additional embodiment, the component comprises an organ.

For any of the foregoing embodiments, in an additional embodiment, the organ is selected from the group consisting of a skin, a brain, a meninx, an artery, a vein, an eye, an optic nerve, a cochlea, an olfactory nerve, an oculomotor nerve, a trochlear nerve, a trigeminal nerve, an abducent nerve, a facial nerve, a vestibulocochlear nerve, a glossopharyngeal nerve, a vagus nerve, a spinal accessory nerve, a hypoglossal nerve, a brainstem, a spinal cord, a nerve root, a neuron, a bone, a muscle, a nasopharynx, an oropharynx, an esophagus, a stomach, a duodenum, a jejunum, an ileum, a colon, a rectum, an anus, a heart, an aorta, a femoral artery, a popliteal artery, a common carotid artery, an internal carotid artery, a capillary, blood, a thymus, a thyroid, a parathyroid gland, an adrenal gland, a pituitary gland, a kidney, a lung, a trachea, a brochiole, an alveolus, a pancreas, a hand, an arm, a forearm, a leg, a foot, a thigh, a ligament, a tendon, a cartilage, connective tissue, a hair follicle, a liver, a lymph node, a gallbladder, a bile duct, a lymphatic duct, a tongue, a spleen, a ureter, a urethra, a prostate, a uterus, an ovary, a testis, a fallopian tube, a reproductive organ, or a bladder, or any combination thereof.

For any of the foregoing embodiments, in an additional embodiment, the component comprises a neoplasm.

For any of the foregoing embodiments, in an additional embodiment, the biological sample comprises a neoplasm.

In any of the foregoing embodiments, an additional embodiment further includes collimating the irradiation.

In any of the foregoing embodiments, an additional embodiment further includes focusing the irradiation onto a target.

For any of the foregoing embodiments, in an additional embodiment, the target receives substantially all of the FIR irradiation.

For any of the foregoing embodiments, in an additional embodiment, the target has a diameter in the range of about 1 micron to about 2 meters.

For any of the foregoing embodiments, in an additional embodiment, the target has a diameter in the range of about 1 micron to about 1 millimeter.

For any of the foregoing embodiments, in an additional embodiment, the target has a diameter in the range of about 10 microns to 100 microns.

For any of the foregoing embodiments, in an additional embodiment, the target has a diameter in the range of about 100 microns to 1 millimeter.

For any of the foregoing embodiments, in an additional embodiment, the target has a diameter in the range of about 1 centimeter to about 10 centimeters.

For any of the foregoing embodiments, in an additional embodiment, the target comprises a microarray.

In any of the foregoing embodiments, an additional embodiment further includes positioning the biological sample proximate to a distal end of a waveguide, and directing the irradiation through the waveguide to the biological sample.

For any of the foregoing embodiments, in an additional embodiment, the waveguide further comprises a proximal end, and a diameter of the waveguide decreases from the proximal to the distal end.

For any of the foregoing embodiments, in an additional embodiment, the diameter of the waveguide decreases from about 1 cm at the proximal end to about 50 microns at the distal end.

For any of the foregoing embodiments, in an additional embodiment, the waveguide further comprises a reflective coating on an inner surface of the waveguide.

For any of the foregoing embodiments, in an additional embodiment, the reflective coating is selected from the group consisting of aluminum, silver, or gold, or any combination thereof. The aluminum, silver, or gold may also be alloyed with appropriate metals, such as with chromium or tin.

For any of the foregoing embodiments, in an additional embodiment, wherein the FIR irradiation is provided by a source, the source including resonator means for defining a resonant cavity in which stimulated radiation can propagate to generate coherent electromagnetic laser radiation, the resonator means including at least a first diffraction grating means for defining a geometrically periodic coupling structure, means for directing a beam of electrons over the diffraction grating means to excite an electromagnetic field through which the electron beam propagates, the beam of electrons having a beam thickness selected relative to the wavelength of the coherent electromagnetic laser radiation, and the grating means and the beam directing means being adapted to produce interaction between the beam and the electromagnetic field for generating stimulated radiation, so that the stimulated radiation propagates in the resonant cavity to generate coherent electromagnetic laser radiation.

For any of the foregoing embodiments, in an additional embodiment, the FIR irradiation is provided by a source, the source including a source of a beam of electrons, diffraction grating means, means for directing a beam of electrons along a path extending over the grating means so that the beam interacts with the grating to produce interaction electromagnetic radiation, at least a first mode of the interaction electromagnetic radiation being directed along a selected axis substantially parallel to the path of the beam, resonator means for providing feedback of at least the first mode of the interaction electromagnetic radiation, and means for controlling the current of the beam of electrons for selectively increasing the current at least up to a feedback beam current level to provide feedback from the resonator means of at least the first mode of the interaction electromagnetic radiation for achieving the stimulated radiation.

For any of the foregoing embodiments, in an additional embodiment, wherein removing includes removing substantially all X rays.

For any of the foregoing embodiments, in an additional embodiment, the filter comprises an off-axis collimating reflector.

For any of the foregoing embodiments, in an additional embodiment, the collimating reflector is sized, shaped, and positioned to remove X-rays from the irradiation.

For any of the foregoing embodiments, in an additional embodiment, the filter comprises a first mirror.

For any of the foregoing embodiments, in an additional embodiment, the first mirror is sized, shaped, and positioned to remove X-rays from the irradiation.

For any of the foregoing embodiments, in an additional embodiment, a reflective surface of the first mirror is flat.

For any of the foregoing embodiments, in an additional embodiment, a reflective surface of the first mirror is curved.

In any of the foregoing embodiments, an additional embodiment further includes a second mirror.

For any of the foregoing embodiments, in an additional embodiment, the filter comprises an electrostatic decelerating grid.

In any of the foregoing embodiments, an additional embodiment further includes a sample cell, receiving the irradiation from the filter.

For any of the foregoing embodiments, in an additional embodiment, wherein the sample cell is selected from the group consisting of polymethylpentene, polyester, polypropylene, polyethylene, single crystal quartz, styrene, or sapphire, or any combination thereof.

For any of the foregoing embodiments, in an additional embodiment, the sample cell contains a biological sample.

For any of the foregoing embodiments, in an additional embodiment, the irradiation is tuned to couple selectively with a component of the biological sample.

For any of the foregoing embodiments, in an additional embodiment, the detector emits spectroscopic data in response to the residual quantity of the irradiation.

For any of the foregoing embodiments, in an additional embodiment, the detector emits image data in response to the residual quantity of the irradiation.

For any of the foregoing embodiments, in an additional embodiment, at least one of a power of the irradiation, a wavelength of the irradiation, a duration of the irradiation, a pulse rate of the irradiation, a pulse shape of the irradiation, a duty cycle of the irradiation, or a bandwidth of the irradiation is determined at least in part in response to feedback from an assay.

For any of the foregoing embodiments, in an additional embodiment, the source and the filter are disposed in a common housing.

For any of the foregoing embodiments, in an additional embodiment, the common housing comprises an output window.

For any of the foregoing embodiments, in an additional embodiment, the common housing comprises an output lens.

For any of the foregoing embodiments, in an additional embodiment, the output lens collimates the irradiation.

Certain embodiments provide systems and methods for the generation and the application of FIR band electromagnetic radiant energy onto biological matter with minimal contamination by energy from other bands in the electromagnetic spectrum.

In certain embodiments, the presently disclosed subject matter provides devices, apparatuses, methods, assays, and processes for the generation, filtration, delivery to biological matter, and detection of FIR band radiant energy with minimal contamination by radiation from other bands of the electromagnetic spectrum.

In certain embodiments, the presently disclosed subject matter provides devices, apparatuses, methods, assays, and processes for applying FIR band electromagnetic radiation to biological matter with minimal contamination by radiation from other bands of the electromagnetic spectrum.

In one embodiment, at least one of the disclosed devices, apparatuses, methods, assays, and processes includes an FIR source producing an FIR irradiation, a filter receiving the irradiation from the source, a sample cell receiving the irradiation from the filter and containing a biological sample, and optionally, a detector, receiving a quantity of the irradiation from the sample cell.

In an embodiment, a pellicle or thin film beamsplitter is placed in the beam before the sample. The beam splitter diverts a fraction of the beam to a detector for monitoring. Monitoring can take place before the sample or after or both.

In a related embodiment, the FIR source produces an irradiation with a power in the range of 1 picoWatt to 1 Watt, a wavelength in the range of 10 microns to 3000 microns, and a bandwidth of 0.01 $cm^{-1}$ to 100 $cm^{-1}$.

In another related embodiment, the filter comprises an off-axis parabaloid collimating reflector and at least one mirror.

In yet another related embodiment, the sample cell is at least one of polymethylpentene, polyester, polypropylene, polyethylene, single crystal quartz, styrene, and sapphire.

In another embodiment, at least one of the disclosed devices, apparatuses, methods, assays, and processes provides a method for irradiating a biological sample with FIR radiation, comprising the steps of providing an FIR irradiation device as described in the first embodiment above, suspending a biological sample in an aqueous solution and/or aqueous gel, placing the solution containing the sample in the sample cell of the irradiation device, causing the FIR source to produce the irradiation, and allowing the sample to receive the irradiation.

A related embodiment further comprises the step of subjecting the sample to an assay.

Another related embodiment further comprises the step of receiving a quantity of FIR radiant energy by the detector.

FIR irradiation can be provided and/or detected at the same frequency as the original source, or might be at any other frequency within the electromagnetic spectrum, e.g. as the result of fluorescence type effects.

In another embodiment, FIR of selected wavelengths is delivered to biological matter comprising living cells.

In another embodiment, FIR of selected wavelengths is delivered to biological matter comprising proteins within living cells.

In another embodiment, FIR of selected wavelengths is delivered to biological matter comprising cytoskeletal proteins within living cells.

In another embodiment, FIR of selected wavelengths is delivered to biological matter comprising nucleic acids within living cells.

In another embodiment, FIR of selected wavelengths is delivered to biological matter comprising deoxyribonucleic acids within living cells.

In another embodiment, FIR of selected wavelengths is delivered to biological matter comprising ribonucleic acids within living cells.

In another embodiment, FIR of selected wavelengths is delivered to biological matter comprising proteins isolated from living cells.

In another embodiment, FIR of selected wavelengths is delivered to biological matter comprising cytoskeletal proteins isolated from living cells.

In another embodiment, FIR of selected wavelengths is delivered to biological matter comprising nucleic acids isolated from living cells.

In another embodiment, FIR of selected wavelengths is delivered to biological matter comprising deoxyribonucleic acids isolated from living cells.

In another embodiment, FIR of selected wavelengths is delivered to biological matter comprising ribonucleic acids isolated from living cells.

In another embodiment, FIR of selected wavelengths is delivered to biological matter comprising a tissue of a human or animal organism.

In another embodiment, FIR of selected wavelengths is delivered to a site within a human or animal organism.

Another embodiment provides a method for treating blood or blood products, comprising removing temporarily blood or blood products from a subject, exposing the blood or blood products to FIR radiant energy of selected wavelengths to induce changes in the biological matter within the blood, and returning the blood or blood products to the subject. Such an embodiment may be practiced in a continuous fashion, i.e., the blood or blood products are continuously pumped out of the body, through a fixture providing exposure to an effective amount of FIR radiant energy, and back into the body.

BRIEF DESCRIPTION OF THE DRAWINGS

FIGS. 2A-1 and 2A-2 depict top and front views, respectively, of an instrument according to an embodiment for delivery of FIR radiation to biological matter.

FIGS. 2B-1 and 2B-2 depict top and front views, respectively, of an instrument according to an embodiment for delivery of FIR radiation to biological matter.

FIGS. 5A and 5B depict front and side views, respectively, of an instrument according to one embodiment for delivery of FIR radiation to biological matter.

DETAILED DESCRIPTION

Figure 1:
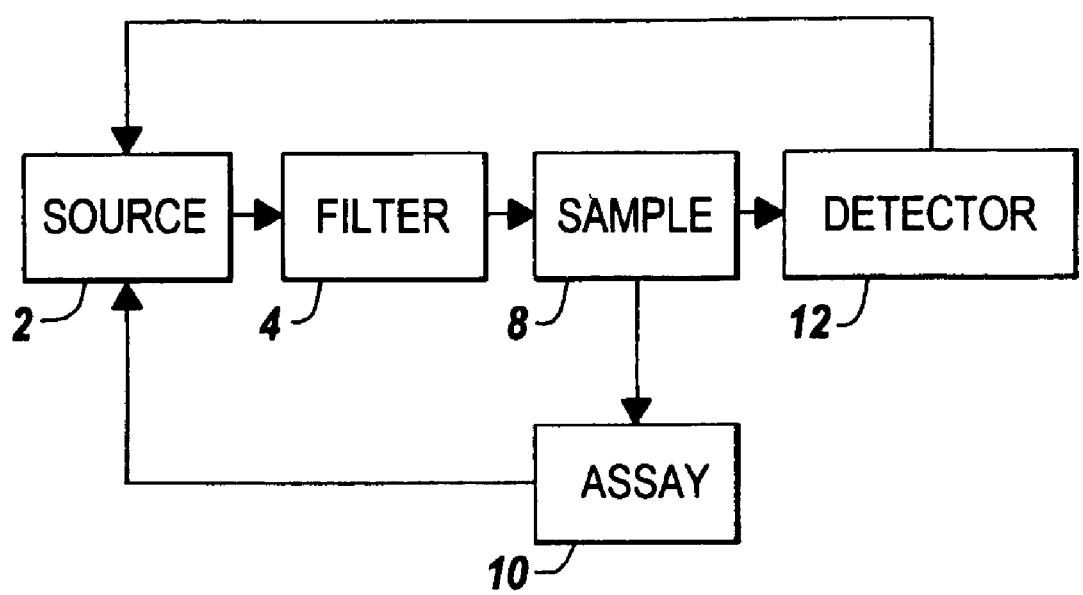
FIG. 1 depicts a functional block diagram according to one embodiment for delivery of FIR radiation to biological matter.

As understood herein, the term "biological matter" refers to any living organism and any substance found within, purified from, or derived from any living organism, or any substance synthesized in vitro to recapitulate or resemble any substance found within, purified from, or derived from any living organism.

The FIR source has several important features. First, it offers continuous tunability, so that any and every frequency in the FIR band may be produced and used, continuous control of bandwidth (or continuous control of the degree of monochromaticity), so that any arbitrary bandwidth from 0.01 $cm^{-1}$ to 100 $cm^{-1}$ could be produced and used, continuous control of the pulse shape, width and repetition rate, and continuous control of the power level from 1 picoWatt to 1 Watt. As understood herein, "continuous" means that the value of a parameter (frequency, bandwidth, pulse shape, width or repetition rate, duty cycle, or power level) can be set to any arbitrary value within an implied or expressed range of values. The source can also produce continuous-wave (CW) output, which corresponds to a 100 per cent duty cycle, although in some embodiments, a smaller duty cycle may be preferred. That any combination of parameters can be used is important because this means that in principle all biological effects can be addressed. Continuous tunability facilitates accessing biological effects, since all frequencies in the band may be reached. Thus, one or more of the FIR frequencies associated with a particular biological effect may be achievable and the effect in question will be accessible to the technology.

In order for vibrations at FIR frequencies to influence the function of biomolecules, it is understood that there must be a physical mechanism by which these vibrations can be induced in proteins and other biomolecules. At least one of the herein disclosed devices, apparatuses, methods, assays, and processes provides such a mechanism. An embodiment according to at least one of the herein disclosed devices, apparatuses, methods, assays, and processes generates electromagnetic radiation in the FIR band that may be tuned, removes radiation from other electromagnetic bands, for example, by filtration, delivers the radiation to biological matter, detects a portion of the radiation during delivery, and analyzes the biological matter for any changes resulting from irradiation. An embodiment according to at least one of the disclosed devices, apparatuses, methods, assays, and processes may induce specific changes in the function or activity of any article of biological matter in a tuned or resonant fashion.

Practices of the disclosed devices, apparatuses, methods, assays, and processes can analyze, test, modify, and treat the biological material as a result of such application of FIR electromagnetic energy, among other scientific and commercial applications.

An embodiment according to at least one of the disclosed devices, apparatuses, methods, assays, and processes may induce such changes because the FIR band radiant energy delivered to the biological matter will be converted into vibrational phonon energy at a frequency the same as or related to the incident FIR radiation. This vibrational energy in the FIR frequency range is received, stored and retransmitted by biomolecules, in particular by the microtubule and actin based structures of the cytoskeleton and/or associated proteins and molecules which have been shown to permeate all living organisms. (For a non-specialist's description of the cytoskeleton and of microtubules, see Ingbar D E, "The architecture of life," *Scientific American*, January 1998).

It has been reported that single-wall carbon nanotubes support a quantized spectrum of phonon vibrations in the FIR frequency range (Hone J et al, "Quantized phonon spectrum of single-wall carbon nanotubes," *Science*, Vol. 289, 8 September 2000, p. 1730). A similar effect can occur in microtubules due to the similarity of microtubules to carbon nanotubes.

An embodiment according to at least one of the disclosed devices, apparatuses, methods, assays, and processes may be used to induce phonon vibrations or modify existing phonon vibrations in biological matter. Such vibrations in the FIR frequency range are sustained by and can be transmitted through the cytoskeleton. Research cited above suggests that much of the information and energy transfer in living organisms is effected through this support by, and transmission through, the cytoskeleton of phonon vibrations in the FIR frequency range. Furthermore, an embodiment according to at least one of the disclosed devices, apparatuses, methods, assays, and processes may modify other biomolecules directly or indirectly interacting with the cytoskeleton elements (including but not limited to centrioles, nuclear lamins, filaments, neurofilaments, DNA, RNA, lipids, fatty acids, triglycerides, phospholipids, steroids, polyisoprenoids, glycolipids, peptides, polypeptides, amino acids, amino acid-coupled transfer RNA, nucleotides, nucleosides, proteins, heat shock proteins, histones, enzymes, lipoproteins, monosaccharides, disaccharides, polysaccharides, lipopolysaccharides, and proteoglycans, glycoproteins, microtubules, microfilaments, and all monomer substituents of these molecules). Biomolecules may be naturally derived or synthesized.

Such modification induced by an embodiment according to at least one of the disclosed devices, apparatuses, methods, assays, and processes may variously effect resonant energy transfer within and throughout a living organism via the cytoskeleton and the organized clusters of water molecules (which clusters may or may not also be adjacent to or intermixed with dissolved ions of K, Na and Ca among other elements) surrounding the cytoskeleton. Such transfers may supply energy for the occurrence, activation of, and deactivation of many of the biomolecular interactions, reactions and processes in a living organism. Such interactions, reactions, and processes include, for example, DNA synthesis and replication, RNA synthesis, protein synthesis, protein degradation, protein folding and conformation, enzymatic activity as a consequence of protein conformation, vesicle transport, carcinogenesis, apoptosis, cell differentiation, cell migration, and cell division (mitosis and meiosis). An embodiment according to at least one of the disclosed devices, apparatuses, methods, assays, and processes may affect a given biomolecule or class of biomolecules selectively by delivering FIR radiation within a specific range of frequencies.

Further applications of the disclosed devices, apparatuses, methods, assays, and processes are contemplated. For example, the FIR irradiation may be focused upon a neoplasm, such as a benign or malignant tumor, to ablate the tumor. Alternatively, imaging and/or spectroscopic data may be obtained from living tissue to detect and localize neoplastic tissue by identifying particular spectral characteristics in FIR imaging or spectral data that distinguish the neoplastic tissue from normal tissue. In an embodiment, such a device could be positioned outside an organism to detect, e.g., tumors, located within the organism.

Applications of the disclosed devices, apparatuses, methods, assays, and processes to geophysics are contemplated. For example, FIR irradiation may be used to detect ground faults and other types of structures, such as bodies of water or particular rock types. FIR irradiation may be used to detect clouds and the presence, type, composition, and propensity to rain of the clouds. Further, FIR may be used to perturb organized water in clouds, thereby causing rainfall. For example, millimeter-sized microdroplets of structured water in clouds may be disrupted by application of FIR irradiation, thereby causing rainfall.

One possible use of FIR radiation is in the triggering of biological processes. Many biological processes appear to be mediated by phase-transitions. An hypothesis has been put forth, supported by appreciable evidence, that the phase-transition is, in fact, a generic mechanism underlying basic cell function (Pollack, 2001). Within this paradigm, an organelle carries out its fiction through the phase-transition. Phase-transitions can involve interaction between solute and solvent, so if FIR radiation affects the solvent, e.g., perturbs water from a structured to a disordered state, either by interacting directly with the water, or by interacting with proteins in such a way that the proteins perturb the water, it will inevitably shift the phase-transition equilibrium. Hence, FIR radiation could be a useful approach to trigger any of a number of intracellular processes, such as intracellular signaling.

Of many examples, a practical one is that of cancer cells. Cell division involves a sequence of sub-processes, each of which is thought to involve some kind of phase-transition. If any one of these sub-processes could be blocked, division might be inhibited. Thus, focused FIR radiation could be used to block the growth of tumors. With disclosed devices, apparatuses, methods, assays, and processes, the frequency and pulse width could be selected to optimize the result.

Another illustrative example is in the area of muscle contraction. In dystrophic disease states, muscles progressively lose their ability to contract. Both the triggering of contraction and the contractile event appear to involve phase-transitions. Hence, contraction should be triggerable by an FIR source. Currently, this is done by electrodes, but the triggering current is rather diffuse. A focused FIR source, optimally tuned, could be used to trigger local contraction, thereby "exercising" the target muscle and increasing its vigor. Particular molecular targets within the muscle can include, e.g., actin, myosin, titin, troponin, and tropomyosin. Myosin can cause water destructuring by using energy from hydrolysis of ATP. In hydrolizing ATP, myosin can vibrate to destructure the water. Other proteins in contact with the myosin, such as actin, tropomyosin, dystrophin, and alpha actinin, may also establish vibrations that destructure water. The water may be vicinal water. In neurons, neurofilaments and spectrin can vibrate, thereby destructuring water.

Another biological example is in the artificial release of drugs. In smart drug-delivery systems, the active substance is typically embedded in a gel. When the gel undergoes a phase-transition, and becomes permeable, the substance is released. Release could therefore be triggered by an FIR pulse. The gel could be designed such that the drug is responsive to radiation at a particular frequency, thereby allowing specificity of release targets.

In additional embodiments, FIR irradiation can be delivered to DNA within living cells where the DNA is in the form of chromatin. FIR irradiation can be delivered to centrioles within living cells. FIR irradiation can be delivered to living cells in order to modify the activity of the DNA. FIR irradiation can be delivered to living cells in order to modify rate of DNA replication. FIR irradiation can be delivered to living cells in order to modify rate of DNA transcription into RNA.

FIR irradiation can be delivered to living cells in order to modify rate of progress of cell mitosis. FIR irradiation can be delivered to living cells in order to modify the process of morphogenesis of an organism. FIR irradiation can be delivered to living cells in order to modify the cells' rate of progress of cell mitosis. FIR irradiation can be delivered to living cells in order to modify the DNA rearrangement process during antibody generation. FIR irradiation can be delivered to cytoskeleton elements including, e.g., microtubules and actin fibers within living cells in order to modify transfer of cellular components along these elements. FIR irradiation can be delivered to neurons within living organisms in order to modify the activity of the neurons. FIR irradiation can be delivered to the olfactory system within living organisms in order to modify the organisms ability to smell.

FIR irradiation can be delivered to living cells in order to modify the rate of cell division. FIR irradiation can be delivered to living cells in order to modify the rate of low level photon emission in visible frequencies (e.g., 300–800 nm wavelength). FIR irradiation can be delivered to living cells in order to modify the rate of low level photon emission in visible frequencies (e.g., 300–800 nm wavelength) in order to determine the health of the cells. FIR irradiation can be delivered to DNA and centrioles within living cells in order to modify a Bose Einstein condensate of phonons in the centriole and DNA of a living cell.

The disclosed devices, apparatuses, methods, assays, and processes can facilitate the induction of resonant effects in some system at a specific frequency.

The disclosed devices, apparatuses, methods, assays, and processes contemplate techniques to facilitate drug discovery. Compounds may be screened for sensitivity to particular FIR frequencies shared by a target molecule. Similar or related frequencies may suggest similar chemical and/or physical properties shared by the target and the compound. For example, the FIR sensitivities of drugs or drug targets could be noted, and then a library of compounds could be screened to find similar sensitivities among candidate drugs or targets. Alternatively, binding strength and/or binding kinetics between candidate drugs and targets could be determined by measuring how much FIR irradiation of a selected frequency is necessary and/or sufficient to disrupt the binding of a drug candidate to a target. In another alternative, FIR irradiation can be used to monitor the catalytic rate of an enzyme, by detecting a conformational or phase change in the enzyme, a cofactor, a reactant, or a product.

In an embodiment, a waveguide can be provided to deliver the FIR irradiation to an area smaller than the diffraction limit typical for FIR wavelengths. The FIR beam can be introduced into the proximal end of the waveguide, the proximal end having a diameter in one embodiment of about 1 cm. The inside of the waveguide is preferably coated with a reflective coating (e.g. aluminum, silver, and/or gold). The waveguide can be drawn (in, e.g., a flame) so that it gradually tapers from, e.g., 1 centimeter diameter down to, e.g., about a tenth of a wavelength in diameter at the distal end. In an embodiment, the distal end diameter can be about 50 microns. A target placed right at the tip of the waveguide is impinged upon by the "near field" of the FIR irradiation, which is evanescent from the tip of the waveguide. In this exemplary embodiment, the FIR energy is concentrated to a small target diameter. One can use the energy in the evanescent field to measure absorption by the target sample at the frequency of the FIR field. One can also use the FIR energy in the near filed at the tip of the waveguide to influence a resonant system within the target sample.

This type of delivery system allows delivery of FIR energy to areas with, e.g., up to ten times smaller diameter than the diameter of focus allowed by the diffraction limit. Thus for wavelengths around 500 microns, the FIR irradiation can be concentrates to a spot with a diameter of about 50 microns. This exemplary embodiment could greatly enhance the localization of the delivery of the FIR energy to a biological sample.

In an embodiment, such highly concentrated localization could facilitate Photo Dynamic Therapy (PDT). Normally PDT uses visible or near infrared light from a laser to interact with a dye which has been injected in, e.g., a tumor. The light is absorbed preferentially by the dye which has been preferentially taken up by the tumor so that any heating induced by the absorption of the laser light is in the tumor. In principle, this would kill the tumor while having little effect on surrounding tissue. In an embodiment, a tumor having a resonant frequency in the FIR band that is not shared by normal tissue or is substantially weaker in normal tissue, could be ablated by delivery of concentrated FIR selectively to the tumor. Delivery would be selective, e.g., because the normal is not sensitive to the chosen frequency of FIR irradiation.

In an embodiment, FIR irradiation may be applied to an enzyme to increase the reaction rate of the enzyme, or to substitute for a cofactor, reactant, or intermediate during the enzymatic reaction. Increasing reaction speed or efficiency can facilitate protein expression and may increase the yield of product for a given amount of enzyme or within a given period of time. Conversely, FIR irradiation may be delivered to an enzyme to impede its reaction, thereby providing a method to, e.g., control a process or prevent formation, maintenance, or progression of a disease.

In an embodiment, FIR irradiation of a sample can provide a "fingerprint" of the sample by identifying particular FIR frequencies or sub-bands to which the sample is sensitive. Thus, the presence of one article may be detected with another article, if the two articles differ in their FIR spectra.

In an embodiment, apertures of the optical elements can be smaller than those used with microwaves. In an embodiment, reflective elements for practice of the disclosed devices, apparatuses, methods, assays, and processes, are preferentially adapted for use with FIR irradiation. In an embodiment, reflective elements for practice of the disclosed devices, apparatuses, methods, assays, and processes, are preferentially adapted for use with FIR irradiation may be those designed for use with radiation from other regions of the spectrum, such as with visible light.

In an embodiment, at least one of the disclosed devices, apparatuses, methods, assays, and processes, provides a filter to remove X rays. When a high energy electron beam (for example, a beam having an energy of 30 KeV (30,000 electron Volts) impinges on and is stopped or slowed by some material (i.e. the grating or the walls of a chamber) x-rays can be emitted as a result. The energy of the high speed electrons can be dissipated in the form of, e.g., x-radiation or heat. X rays thereby produced can contaminate the irradiation produced by directing the electron beam past, e.g., a grating. The x-ray contamination can interact with, e.g., an operator, an observer, or the article to which the irradiation is directed. The x-rays may cause damage, especially if they contact biological matter. Therefore, the disclosed devices, apparatuses, methods, assays, and processes, contemplate filters for removing x-rays from the FIR irradiation.

In an embodiment, an electrostatic decelerating grid is provided to receive the electron beam and to dissipate the energy of the electrons without generating x-rays. In another embodiment, the FIR irradiation is directed away from its origin through a "maze" or convoluted optical path. The maze may located inside a common housing with the FIR source. For example, the filter may be positioned inside the vacuum chamber that contains the grating and the region of interaction between the electron beam and grating. In an embodiment, the filter may be located outside the housing. In an embodiment, the filter may be located partly inside the housing and partly outside the housing. In an embodiment, the housing may include a part of the filter.

In an embodiment, the filter includes one or more mirrors. In an embodiment, the mirrors can reflect FIR while blocking x-rays. X rays impinging on a mirror may give rise to secondary (or tertiary, etc.) x-rays, which can then propagate in a direction different from that of the FIR irradiation, thereby removing the x-rays from the FIR irradiation. A second mirror repeating the process can facilitate the removal of x-rays from the FIR irradiation.

In an embodiment, the mirror is sized with sufficient thickness to stop the x-rays. In an embodiment, the mirror includes a material having a density sufficient to stop x-rays. In an embodiment, the mirror includes at last one of lead or aluminum. In an embodiment, reflective surfaces are applied to the at least one of lead or aluminum. In an embodiment, the reflective surface comprises aluminum.

As described herein, the mirrors, including flat mirrors and curved mirrors, can be used to create a path change for the FIR irradiation that excludes X-rays. X-rays may not reflect from surfaces, and can create secondary X-rays of lower energy that are related to the surface from which they emit. More surfaces may further reduce the chance that energetic X-rays will be able to follow the FIR irradiation. In an embodiment, one mirror surface is provided. In an embodiment, two mirror surfaces are provided. In an embodiment, three mirror surfaces are provided. In another embodiment, more than three mirrors are provided.

As described herein, the mirrors, including flat mirrors and curved mirrors, can be used to act as focusing elements with cylindrical, spherical or parabolic surfaces. Combinations of variously sized and shaped mirrors can be used to create the desired beam shape. In an embodiment, the FIR irradiation beam can be emitted from the grating divergently at about, e.g., f=5, but may be astigmatic, having different f numbers in different axes. The beam could be made divergent, collimated, convergent, asymmetric (having astigmatism). In an embodiment, the mirror system can be sufficiently small to be contained within the vacuum chamber. Sizing the mirror system small enough to fit within a small vacuum chamber can help avoid requiring a large vacuum pump to maintain a typical vacuum chamber pressure of about $1 \cdot 10^{-6}$ Torr and thereby keep the laser system, in an embodiment, small and/or compact. In an embodiment, the vacuum chamber can contain the grating and also the mirrors and be about 2 cc to about 5 cc in volume.

As described herein, the mirrors, including flat mirrors and curved mirrors, can be fabricated from, e.g., metals or substrates covered with metals. Materials from which the mirrors can be fabricated include but are not limited to, e.g., aluminum, brass, copper, metalcoated plastic, or glass coated with, e.g., silver or aluminum. In an embodiment, mirrors can have an anti-reflection coating. In an embodiment, mirrors designed for or appropriate for visible light may be used for FIR irradiation. In an embodiment, mirrors placed in the vacuum chamber can be low-outgassing materials.

In an embodiment, a lens can be provided in the optical path of the FIR irradiation. The lenses could be made of any FIR-transparent or semi-transparent material, including but not limited to, polymethylpentene, polyester, polypropylene, polyethylene, single crystal quartz, or sapphire, styrene, or any combination thereof.

In an embodiment, the vacuum chamber has an output window through which the FIR irradiation can leave the vacuum chamber. In an embodiment, the output window can be plano. The output window can be fashioned with any of the materials described above. In an embodiment, the output window can be made from polymethylpentene and can have an electrically conductive coating on the vacuum side that may be transparent to the FIR. In an embodiment, the material from which the output window is made can maintain the integrity of the vacuum inside the vacuum chamber.

In an embodiment, the output window may be any optical element to focus, collimate, diverge, or perform any optical change on the FIR irradiation as described above or known in the art.

In a preferred embodiment, a tunable, narrow-band source is provided. Such a source facilitates driving a resonance of a biological sample or a component thereof because the source can emit FIR irradiation of a specified frequency, power, and bandwidth.

In an embodiment, an FIR source can produce FIR irradiation can have a peak power of about 100 milliwatts per square centimeter. In an embodiment, FIR irradiation having power of about 1 microwatt can be focused on a target having an area of about $10^{-5}$ square cm The figures illustrate equipment for the practice of the disclosed devices, apparatuses, methods, assays, and processes.

FIG. 1 shows a functional block diagram according to an embodiment of the disclosed devices, apparatuses, methods, assays, and processes for the irradiation of biological matter with FIR radiation. A source (2) emits FIR radiation, preferably with a power in the picoWatt to Watt range, preferably with a tunable frequency in the 10 to 3000 micron range, and preferably with a bandwidth in the range from 0.01 cm$^{-1}$ to 100 cm$^{-1}$, more preferably in the range from 0.01 cm$^{-1}$ to 1 cm$^{-1}$, most preferably approximately 0.6 cm$^{-1}$. This radiation is directed through a filter (4) to dissipate or deflect any X-radiation or radiation at any other unwanted frequencies produced as a by-product of the operation of the source (2). The radiation then impinges on a sample of biological material (8). The sample (8) may then be subjected optionally to an assay (10) to measure any changes in the sample (8) induced by the radiation. A detector (12) may be employed optionally to measure any residual radiation following impingement on the sample (8). Feedback may be sent from the detector (12) and/or the assay (10) to the source (2) to modulate or otherwise modify the output of the source (2).

Figure 2:
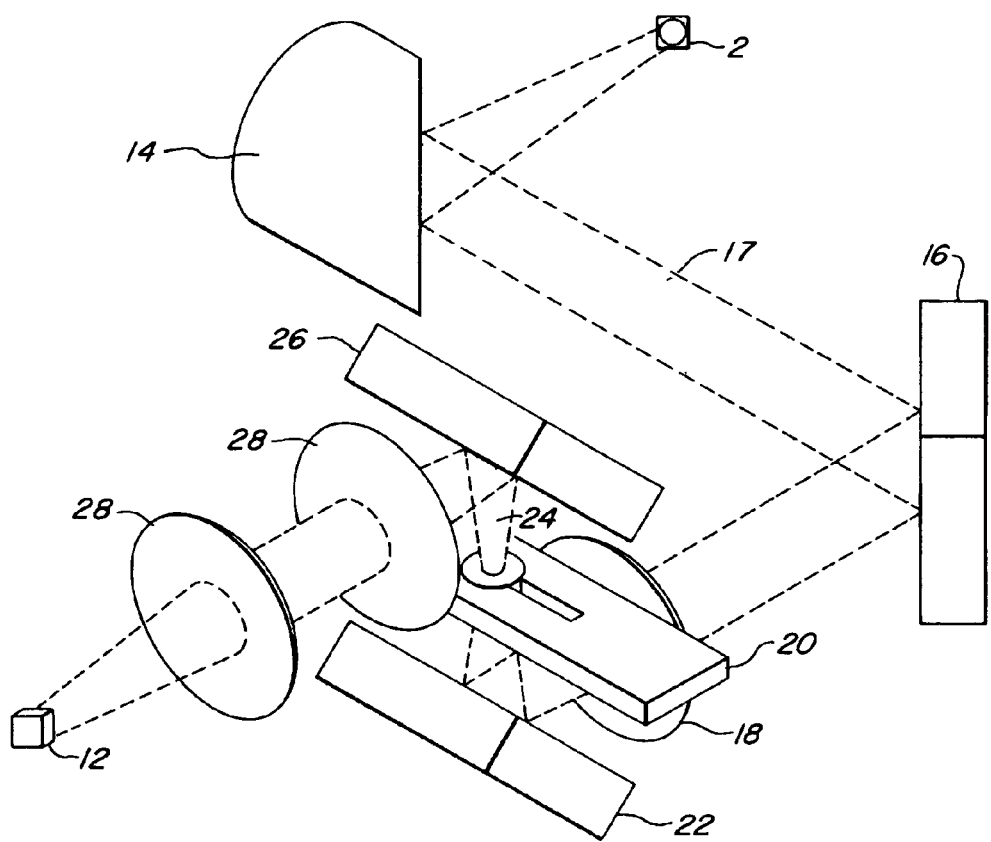
FIG. 2 depicts a projection view of an instrument according to an embodiment for delivery of FIR radiation to biological matter.
Figures 1, 2A:
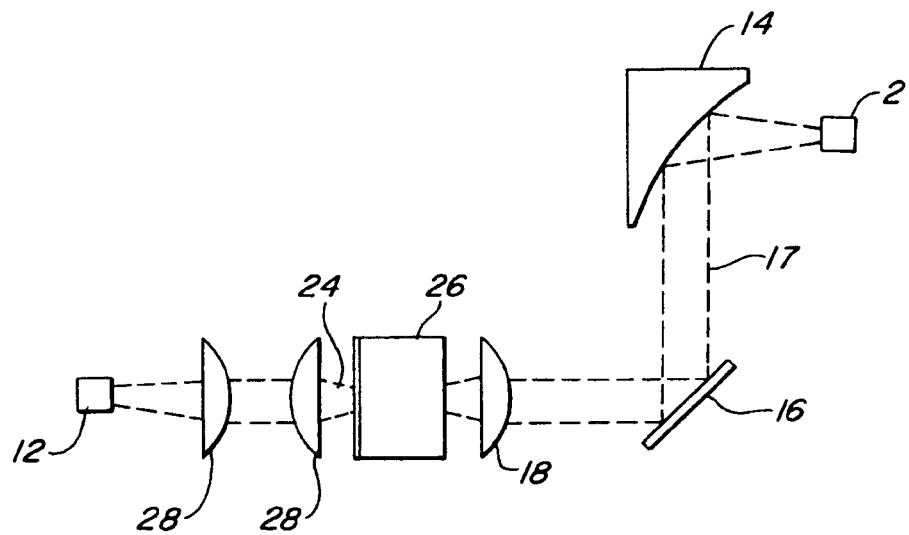
Figures 2, 2A:
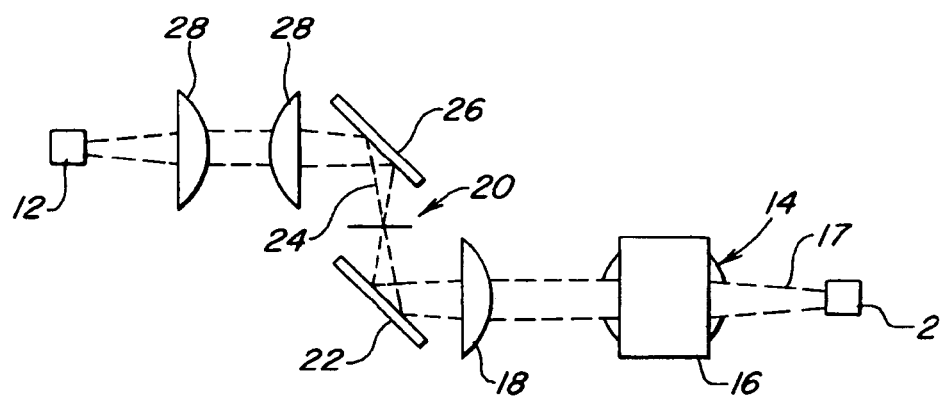

FIG. 2 is an orthogonal projection view of one illustrative embodiment. FIGS. 2A-1 and 2A-2 are top and front views, respectively, of the same embodiment. The FIR source corresponds to the source (2) of FIG. 1. The illustrated filter (4) in FIG. 1 can include by way of example an off-axis parabaloid collimating reflector 14 and a mirror 16, both of which can be in optical alignment with the path of the source output. The radiation 17 can be focused to impinge on the sample in the sample cell 20 by a lens 18. The radiation 17 may be deflected by a second mirror 22. The sample cell 20 may contain the biological matter to be irradiated. A residual radiation 24 (e.g., a portion of the source output not absorbed by the optical components, the sample cell 20, the sample, or the aqueous solution and/or aqueous gel in which the sample may be suspended) may be then reflected by a third mirror 26 and optionally focused by one or more lenses 28 to be detected optionally by the detector 12.

Figures 1, 2B:
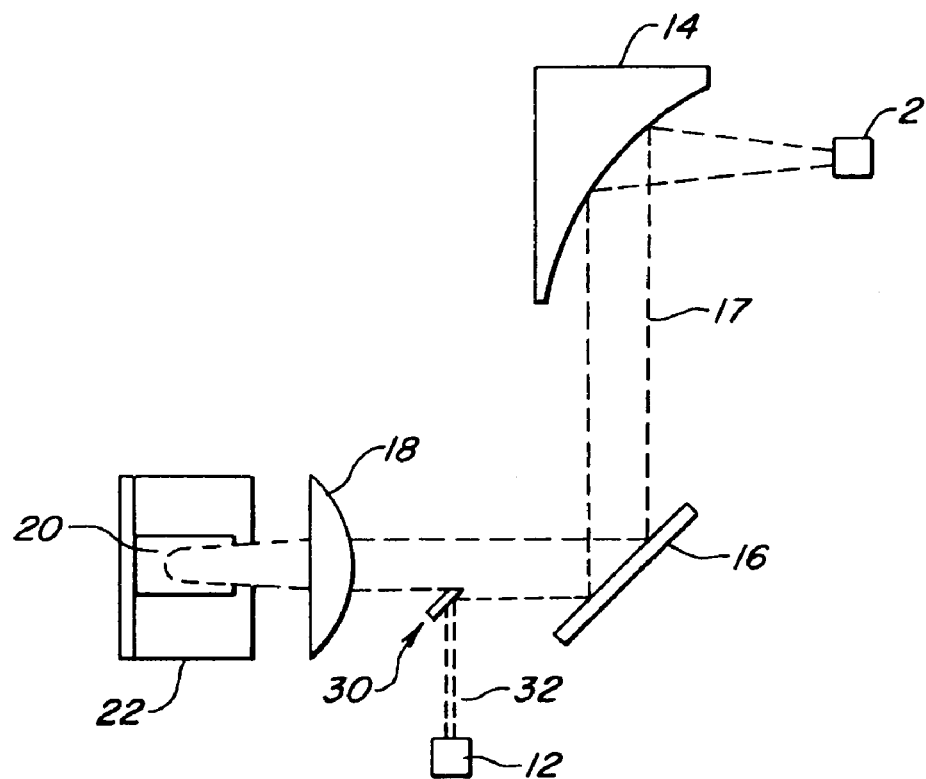
Figures 2, 2B:
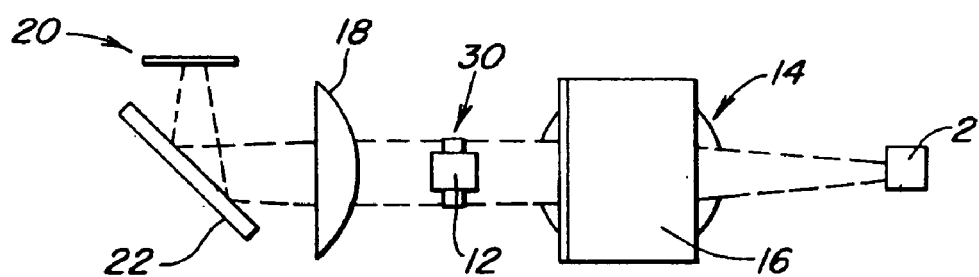

FIGS. 2B-1 and 2B-2 show top and front views, respectively, of an exemplary embodiment in which a mirror 30 deflects a small portion 32 of the source output 17, for example 5%, to the detector 12. Alternatively, a beamsplitter or pellicle could be used to direct a portion of the irradiation to a detector. This has the advantage of removing the detector from the area of the sample to allow more flexibility in engineering the sample area. It may also be used to normalize the output (which varies over time) of the FIR source when using the apparatus to perform absorption spectroscopy.

The FIR source may be directed through a filter comprising by way of example a combination of refractive (i.e., lens) and reflective (i.e. mirror) optical components to a sample target. The system may be optimized to place all FIR available on a target area preferably no larger than about 1 mm in diameter. It is also preferable for the target area to be no larger than the diffraction limit will allow for the wavelengths being used. Such placement minimizes waste of available FIR and also permits selective delivery of FIR to multiple articles of biological matter, to a single article, or even to one portion of an article of biological matter with minimal delivery to other portions of the same article. However, one of ordinary skill in the art would appreciate that the target area size need not be so limited, but may be of any size, given the application. The sample comprises a quantity of biological matter, for example, living cells suspended in an aqueous solution and/or aqueous gel.

The FIR source can be operated continuously or pulsed, illustratively, at about 100 Hz with a 10–15% duty cycle to prevent heating of components within the FIR source and of the biological sample as well as to eliminate the need for a chopper in the optical path. A variety of pulse shapes obvious to those skilled in the art can be employed to enhance the effects of the FIR and/or minimize collateral damage to the target during irradiation.

A device according to an embodiment Of the disclosed devices, apparatuses, methods, assays, and processes may be used to determine experimentally optimal wavelengths for interactions with the targeted cellular components. While the optimum wavelengths for certain cellular components are known in the art, many others are currently being elucidated, and many more have yet even to be investigated. As used herein, "optimum wavelength" refers to a wavelength of FIR radiant energy selected for its ability to elicit the expected or desired effect more quickly or efficiently than other frequencies, for its ability to evade absorption by water and specifically elicit vibrational energy in a specific article of biological matter, or for its ability to induce vibrational energy in water molecules or chains of water molecules as a method to enhance the coupling of the FIR into a specific article of biological matter.

The refractive elements (for example, the lenses 18 and 28) can be made of materials that are in the range of about 50% to 95% transparent to the FIR. Examples of such materials include polyester, polypropylene, polyethylene, polymethylpentene (PMP), styrene, single crystal quartz, and sapphire. PMP has the advantage of being transparent to visible light (VIS) as well as to the FIR, and it also has nearly the same refractive index at both wavelengths. Fabricating the refractive elements with PMP greatly facilitates aligning the FIR optical system with visible light, as well as permitting the sharing of the optical path by both FIR and VIS. This can also permit application of the FIR while simultaneously making VIS observations of the target, or simultaneously applying VIS (lasers, lamps) to the target by similar means such as dichroic mirrors and interference filters such as are currently used for fluorescence microscopy. Sapphire is also transparent to both VIS and FIR, and can be fabricated with optical surfaces suitable for high resolution microscopy, however sapphire in these thicknesses has more absorption losses than PMP. There are other materials (described in the book *Far Infrared Techniques,* by Maurice Kimmitt, Pion Limited, 1970, SBN 85086 009 1) that act as longpass and shortpass filters.

The reflective elements of the optical system of FIG. 2 can be typically made of glass or other ceramics, metals and plastics, as described above. The ceramics and metals are usually aluminized front surface mirrors of the type commonly used in optical systems, however any metal with a surface polished sufficiently to reflect FIR will suffice. An advantage of using optical quality front surface metallized reflectors (plano, concave, convex, paraboloid, parabolic) is that, in combination with, e.g., PMP or sapphire, the whole optical system can be shared by both VIS and FIR as required. Metals can also form grids and screens which are selectively reflective of the FIR depending upon the spatial frequency of the elements of the grid/screen.

Partially reflective elements can be made of most the above materials to be used as beam splitters and/or polarizers, as well as the type of wire grid polarizer/beamsplitter made by Sciencetech in Canada, and others. In an embodiment, a 50% beamsplitter includes a thin polyester sheet (e.g., DuPont Mylar).

Any of the non-conductive optical elements exposed to the electron beam in the FIR source (PMP window in one embodiment, high molecular weight polyethylene in another embodiment) preferably has a conductive coating, more preferably metallic, applied to bleed off any electrical charge that might develop otherwise. A charge build-up can deflect the electron beam and make source operation difficult. Metal coatings can be applied by vacuum deposition, or, alternatively, a weak solution of colloidal graphite suspended in alcohol may be applied to create a layer of conductive carbon that is sufficient to carry any electrons to ground, but not so thick as to interfere with the FIR transmission through the optical element. The graphite works adequately, and is simple to apply.

Figure 3:
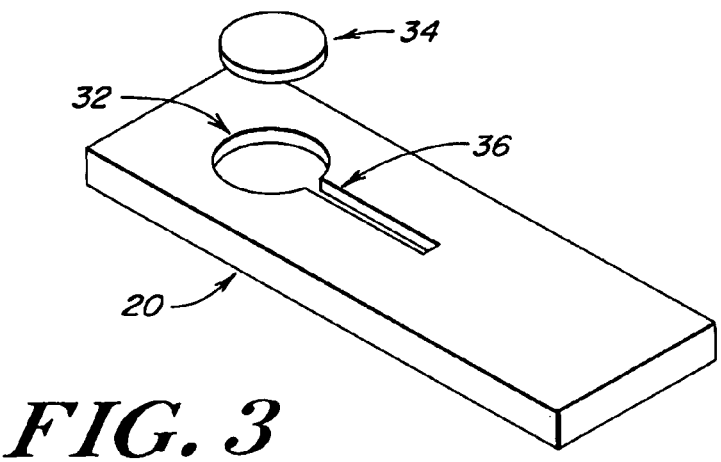
FIG. 3 depicts one embodiment of an apparatus to contain a sample of biological matter during delivery of FIR radiation to the biological matter.

FIG. 3 is an exploded view of the sample cell 20. The sample cell may be a microscope slide composed of a material that is non-toxic to biological matter, transparent or semitransparent to FIR radiation, and, preferably, transparent to both FIR radiation and visible light. Examples include those materials described above as being appropriate for the refractive elements of an embodiment of the disclosed devices, apparatuses, methods, assays, and processes. In the upper surface of the sample cell can be a recessed reservoir 32 for containing an article of biological matter. The reservoir 32 may have a slot 36 to hold fluid. The reservoir 32 may be produced by milling, etching, or any other method familiar to one skilled in the art. The reservoir 32 may be covered by a cover glass 34, comprising a thin wafer of a material which may be transparent to VIS and partially or fully transparent to FIR, preferably sapphire. The sample cell 20 and/or the cover glass 34 themselves may function as additional refractive elements, further focusing the source output on the sample.

Figure 4A:
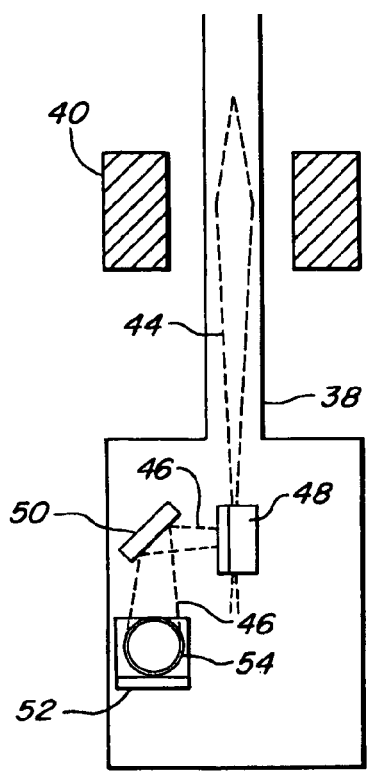
FIGS. 4A and 4B depict front and side views, respectively, of an instrument according to one embodiment for delivery of FIR radiation to biological matter.
Figure 4B:
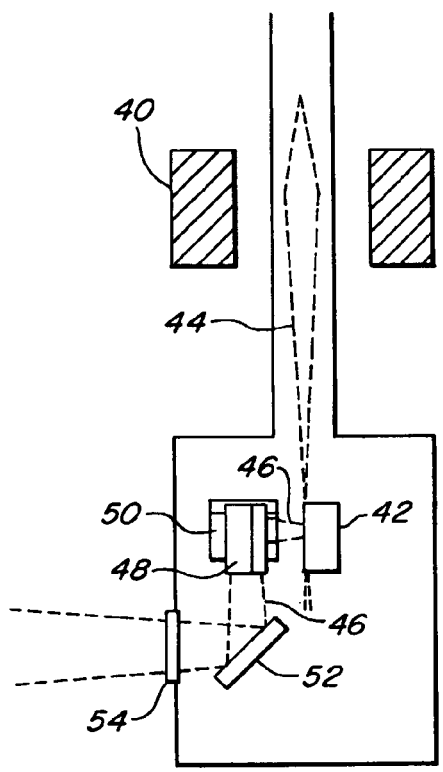

FIGS. 4A and 4B depict front and side views, respectively, of an exemplary embodiment in which the source 2 and filter 4 are contained in a common housing 38. The common housing 38 may be a vacuum chamber. A portion of source 2 is shown, including an electron optical lens 40 and a grating 42. An electron beam 44 is directed past the grating 42, thereby generating output from the grating including FIR irradiation 46. The FIR irradiation 46 can be directed to a first mirror 48, from which it reflects. In the depicted embodiment, the mirror 48 is oriented at 45 degrees relative to the direction of the incident irradiation 46, but one of ordinary skill in the art will recognize that any of the mirrors may be oriented to reflect the irradiation 46 through any angle. The irradiation 46 may optionally be directed to a second mirror 50, and, again optionally, to a third mirror 52. The total number of mirrors is not limited, as described above. The irradiation 46 may then be directed out of the common housing 38 through an output window 54.

In the embodiment depicted in FIGS. 4A and 4B, the mirrors 48, 50, 52, can be piano, or flat, as can be the output window 54.

FIGS. 5A and 5B depict an exemplary embodiment similar to that in FIGS. 4A and 4B except that the output window 54' in this case can be a lens. In an embodiment, output window 54' can collimate the irradiation 46'. In an embodiment, output window 54' can focus the irradiation 46.

Figure 6A:
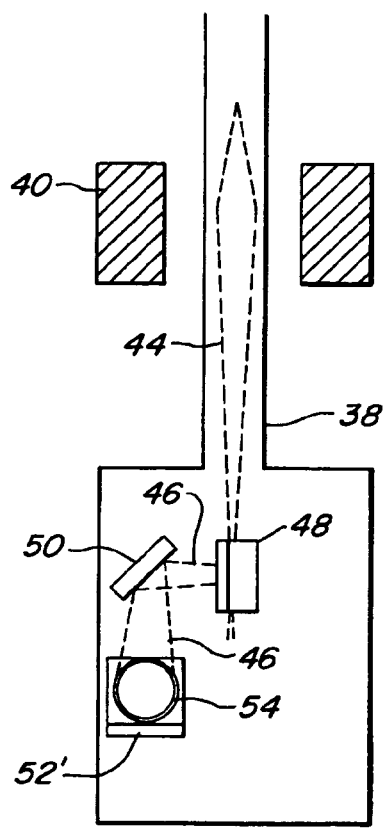
FIGS. 6A and 6B depict front and side views, respectively, of an instrument according to one embodiment for delivery of FIR radiation to biological matter.
Figure 6B:
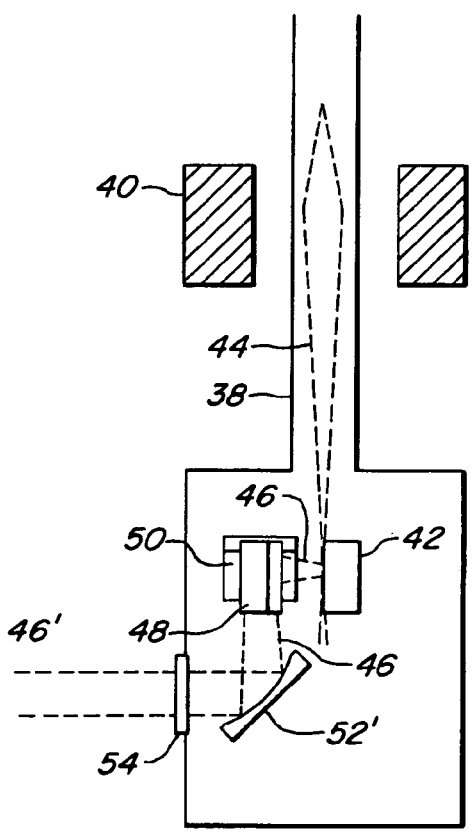

FIGS. 6A and 6B depict an exemplary embodiment similar to that in FIGS. 4A and 4B except that one of the mirrors can be curved. In the depicted embodiment, the third mirror 52' is curved so as to collimate the irradiation 46'. Other mirrors, such as 48 and 50, could be additionally or alternatively curved to, e.g., collimate, focus, correct or induce asymmetry, or any other optical manipulation known in the art.

In an embodiment according to at least one of the disclosed devices, apparatuses, methods, assays, and processes, the biological matter is retained in the sample cell throughout the duration of the irradiation, detection, and assay steps. In another embodiment according to at least one of the disclosed devices, apparatuses, methods, assays, and processes, the biological matter is removed from the sample cell after irradiation and detection and placed in a container more convenient for the assay to be performed. For example, if the sample cell is composed of a material that is not transparent to visible light, then the sample might be moved from the sample cell to a borosilicate glass microscope slide following irradiation to facilitate its examination in a light microscope. Examples of other assay systems with specific container means include but are not limited to nuclear magnetic resonance (NMR), X-ray crystallography, infrared, visible, and/or ultraviolet light spectroscopy, mass spectrometry, fluorescence microscopy, and others.

In one embodiment, the output of the tunable FIR source having a line shape peaked at about the wavelength 445 microns and having a full width at half power of approximately 20 microns, having a duty cycle of 10% and a repetition rate of approximately 100 Hz, and having peak power of approximately 1 microWatt (or a peak signal strength of approximately one volt as detected by a helium cooled silicon bolometer manufactured by Infrared Laboratories operated on the low gain setting of the preamplifier) can be focused on an article of biological matter, for example the surface of an individual green algae multicellular organism of the species *Volvox globator*, held in a reservoir of a sample cell composed of, for example, polymethylpentene. The source output photon energy will be converted to phonon vibrations of a frequency equivalent or related to the output energy frequency in the biological matter or elements of the biological matter therein, inducing changes in the biological matter, for example changes of the transmission and reflection and fluorescence of visible light of specific wavelengths as measured by light spectrospcopy and or fluorescence microscopy.

In an embodiment, contamination in a biological sample or other article can be detected by measuring FIR absorption or emission characteristic of the contaminant but not of the biological sample or other article. In an embodiment, an article can be sterilized by exposing it to FIR irradiation to which the contaminant is sensitive but the article or biological sample is not, or to which the article or biological sample is less sensitive than is the contaminant. This might be particularly useful in places where sterilization or decontamination is important, such as in hospitals or other medical venues, clean rooms, water treatment plants, food processing plants, or in spacecraft.

Measuring binding affinity may include, e.g., determining an affinity or equilibrium constant.

The range of FIR wavelengths used may be from about 10 to 3000 microns, preferably about 100 to 500 microns, most preferably 430 to 480 microns. The range of FIR wavelengths used may be from about 10 microns to about 100 microns. The range of FIR wavelengths used may be from about 100 microns to about 200 microns. The range of FIR wavelengths used may be from about 200 microns to about 300 microns. The range of FIR wavelengths used may be from about 300 microns to about 400 microns. The range of FIR wavelengths used may be from about 400 microns to about 500 microns. The range of FIR wavelengths used may be from about 410 microns to about 420 microns. The range of FIR wavelengths used may be from about 420 microns to about 430 microns. The range of FIR wavelengths used may be from about 430 microns to about 440 microns. The range of FIR wavelengths used may be from about 440 microns to about 450 microns. The range of FIR wavelengths used may be from about 450 microns to about 460 microns. The range of FIR wavelengths used may be from about 460 microns to about 470 microns. The range of FIR wavelengths used may be from about 470 microns to about 480 microns. The range of FIR wavelengths used may be from about 480 microns to about 490 microns. The range of FIR wavelengths used may be from about 490 microns to about 500 microns. The range of FIR wavelengths used may be from about 500 microns to about 600 microns. The range of FIR wavelengths used may be from about 600 microns to about 700 microns. The range of FIR wavelengths used may be from about 700 microns to about 800 microns. The range of FIR wavelengths used may be from about 800 microns to about 900 microns. The range of FIR wavelengths used may be from about 900 microns to about 1000 microns. The range of FIR wavelengths used may be from about 1000 microns to about 2000 microns. The range of FIR wavelengths used may be from about 2000 microns to about 3000 microns.

Duration of irradiation may be in the range from about 1 microsecond to 1 year. The duration of irradiation may be in the range of about 1 second to 1 hour. The duration of irradiation may be in the range of about 1 microsecond to about 10 microseconds. The duration of irradiation may be in the range of about 10 microseconds to about 100 microseconds. The duration of irradiation may be in the range of about 100 microseconds to about 1 second. The duration of irradiation may be in the range of about 1 second to about 2 seconds. The duration of irradiation may be in the range of about 2 seconds to about 3 seconds. The duration of irradiation may be in the range of about 3 seconds to about 4 seconds. The duration of irradiation may be in the range of about 4 seconds to about 5 seconds. The duration of irradiation may be in the range of about 5 seconds to about 6 seconds. The duration of irradiation may be in the range of about 6 seconds to about 7 seconds. The duration of irradiation may be in the range of about 7 seconds to about 8 seconds. The duration of irradiation may be in the range of about 8 seconds to about 9 seconds. The duration of irradiation may be in the range of about 9 seconds to about 10 seconds. The duration of irradiation may be in the range of about 10 seconds to about 1 minute. The duration of irradiation may be in the range of about 1 minute to about 10 minutes. The duration of irradiation may be in the range of about 10 minutes to about 1 hour. The duration of irradiation may be about 3 minutes.

Pulse rate of the irradiation may be in the range of continuous wave to about 1 GigaHertz. Pulse rate of the irradiation may be in the range of continuous wave to about 1 MegaHertz. Pulse rate of the irradiation may be in the range of continuous wave to about 1 kiloHertz. Pulse rate of the irradiation may be in the range of continuous wave to about 100 Hertz (Hz). Pulse rate of the irradiation may be in the range of about 10 Hz to about 100 Hz. Pulse rate of the irradiation may be in the range of about 25 Hz to about 55 Hz. Pulse rate of the irradiation may be about 40 Hz.

In an embodiment of at least one of the disclosed devices, apparatuses, methods, assays, and processes, as illustrated, e.g., in FIGS. 1, 2, the detector comprises a helium cooled bolometer (manufactured by Infrared Laboratories Inc.) to keep track of the FIR signal delivered. Some part of the signal can be absorbed by the optical components, the target, and the aqueous solution and/or aqueous gel; the remainder, typically 10–30% of the FIR is transmitted through the entire fixture/target and is seen by the detector.

In an embodiment of at least one of the disclosed devices, apparatuses, methods, assays, and processes, the filter (4) of FIG. 1 comprises metal reflective surfaces arranged in a labyrinth-like form in the path of the radiation emitted by the source before the radiation impinges on the sample. The filter absorbs and deflects both the primary and secondary X-rays produced by the source electron beam in such a manner as to prevent the X-rays from entering the vicinity of or impinging upon the sample.

Various alternative embodiments are envisioned and within the scope of the disclosed devices, apparatuses, methods, assays, and processes, such as those comprising other FIR sources, arrangements of reflective and refractive elements contained within the filter, types of biological matter subject to FIR irradiation, designs of the sample cell, types and methods of assays to be performed on samples following irradiation, types of detectors, and the like. Therefore, while the disclosed devices, apparatuses, methods, assays, and processes have been particularly shown and described with reference to a number of embodiments thereof, it will be understood by those skilled in the art that various changes in form and details may be made therein without departing from the spirit and scope of the disclosed devices, apparatuses, methods, assays, and processes.

We claim:

1. A method for performing a binding assay, comprising:
    providing tunable FIR irradiation from a source capable of continuous-wave output;
    removing X rays from the irradiation;
    irradiating at least one biological sample with the tunable FIR irradiation from which X rays have been removed;
    providing compounds;
    allowing the biological sample to bind to at least one compound; and
    measuring a binding affinity between the at least one biological sample and the at least one compound.

2. The assay of claim 1, wherein the irradiating disrupts an interaction between the biological sample and the at least one compound.

3. The assay of claim 1, wherein the compounds are provided in a library.

4. A method of detecting an impurity in an article, comprising:
    providing FIR irradiation having a characteristic that is selective for the impurity, the FIR irradiation provided by a source capable of continuous-wave output;
    removing X rays from the irradiation;
    irradiating at least a component of the article with the irradiation from which X rays have been removed; and
    detecting a residual irradiation emitted from at least the component of the article.

5. An imaging method, comprising:
    providing tunable FIR irradiation from a source capable of continuous-wave output;
    removing X rays from the irradiation;
    irradiating at least a component of a biological sample with the irradiation from which X rays have been removed;
    detecting a residual irradiation emitted from at least the component of the biological sample; and
    forming an image of at least the component of the biological sample.

6. A far infrared (FIR) irradiation device, comprising:
    an FIR source producing an FIR irradiation having a tunable wavelength, the source being capable of continuous-wave output; and
    a filter receiving the irradiation from the source and removing X-rays, if any, from the FIR irradiation.

7. The FIR irradiation device of claim 6, wherein the FIR source comprises a free electron laser.

8. The FIR irradiation device of claim 6, wherein the filter comprises an off-axis collimating reflector sized, shaped, and/or positioned to remove X-rays from the irradiation.

9. The FIR irradiation device of claim 6, wherein the filter comprises a first mirror sized, shaped, and/or positioned to remove X-rays from the irradiation.

10. The FIR irradiation device of claim 9, wherein the filter further comprises a second mirror.

11. The FIR irradiation device of claim 6, wherein the irradiation has a pulse shape comprising at least one of rectangular, triangular, sawtooth, sinusoidal, rectified, and constant.

12. The FIR irradiation device of claim 6 wherein the irradiation has continuously tunable power.

13. The FIR irradiation device of claim 6 wherein the irradiation has continuously tunable wavelength.

14. The FIR irradiation device of claim 6 wherein the irradiation has continuously tunable bandwidth.

15. The FIR irradiation device of claim 6 wherein the irradiation has continuously tunable pulse rate.

16. The FIR irradiation device of claim 6 wherein the irradiation has continuously tunable pulse shape.

17. The FIR irradiation device of claim 6 wherein the irradiation has continuously tunable duty cycle.

18. The FIR irradiation device of claim 6 wherein the irradiation has an irradiance in the range of about 1 milliWatt per square centimeter to about 1000 milliWatts per square centimeter.

19. The FIR irradiation device of claim 18, wherein the irradiation has an irradiance of about 100 milliWatts per square centimeter.

20. The FIR irradiation device of claim 6 wherein the irradiation has a power in the range of about 1 picoWatt to about 1 Watt.

21. The FIR irradiation device of claim 20 wherein the irradiation has a power in the range of about 0.1 microWatts to about 10 milliWatts.

22. The FIR irradiation device of claim 6 wherein the irradiation has a wavelength in the range of about 10 microns to about 3,000 microns.

23. The FIR irradiation device of claim 22 wherein the irradiation has a wavelength in the range of about 60 microns to about 1,000 microns.

24. The FIR irradiation device of claim 23 wherein the irradiation has a wavelength in the range of about 100 microns to about 500 microns.

25. The FIR irradiation device of claim 24 wherein the irradiation has a wavelength in range of about 430 microns to about 480 microns.

26. The FIR irradiation device of claim 6 wherein the irradiation has a duration in the range of about 1 microsecond to about 1 hour.

27. The FIR irradiation device of claim 26 wherein the irradiation has a duration in the range of about 100 microseconds to about 1 second.

28. The FIR irradiation device of claim 26 wherein the irradiation has a duration in the range of about 1 second to about 1 minute.

29. The FIR irradiation device of claim 26 wherein the irradiation has a duration in the range of about 1 minute to about 10 minutes.

30. The FIR irradiation device of claim 29 wherein the irradiation has a duration of about 3 minutes.

31. The FIR irradiation device of claim 6 wherein the irradiation has a bandwidth equal to approximately 0.03 times a center wavenumber of the irradiation.

32. The FIR irradiation device of claim 6 wherein the irradiation has a bandwidth in the range of about 0.01 $cm^{-1}$ to about 100 $cm^{-1}$.

33. The FIR irradiation device of claim 32 wherein the irradiation has a bandwidth in the range of about 0.01 cm$^{-1}$ to about 1 cm$^{-1}$.

34. The FIR irradiation device of claim 33 wherein the irradiation has a bandwidth in the range of about 0.6 cm$^{-1}$.

35. The FIR irradiation device of claim 32, wherein the irradiation has a bandwidth in the range of about 1 cm$^{-1}$ to about 100 cm$^{-1}$.

36. The FIR irradiation device of claim 6, wherein the irradiation has a pulse rate in the range from continuous wave to about 1 GigaHertz.

37. The FIR irradiation device of claim 36, wherein the irradiation has a pulse rate in the range from about 25 Hz to about 55 Hz.

38. The FIR irradiation device of claim 6, wherein the irradiation has a duty cycle in the range of about 5 per cent to about 100 per cent.

39. The FIR irradiation device of claim 6, wherein the duty cycle is in the range of about 10 per cent to about 15 per cent.

40. The FIR irradiation device of claim 6, further comprising a sample cell, receiving the irradiation from the filter.

41. The FIR irradiation device of claim 40, wherein the sample cell is formed at least in part of a material selected from the group consisting of polymethylpentene, polyester, polypropylene, polyethylene, single crystal quartz, styrene, sapphire, and any combination thereof.

42. The FIR irradiation device of claim 40 wherein the sample cell is adapted to receive a biological sample.

43. The FIR irradiation device of claim 42 wherein the irradiation is tuned to couple selectively with a component of the biological sample.

44. The FIR irradiation device of claim 43 wherein the component comprises an organelle.

45. The FIR irradiation device of claim 44 wherein the organelle is selected from the group consisting of a nucleus, a cytoskeleton, a centriole, an endoplasmic reticulum, a golgi apparatus, a mitochondrion, a chloroplast, a cell membrane, a nuclear membrane, a cell wall, a lysosome, a vacuole, a vesicle, a ribosome, a peroxisome, and any combination thereof.

46. The FIR irradiation device of claim 43, wherein the component is selected from the group consisting of a mitotic spindle, a DNA polymerase complex, a transcription complex, a protein replication complex, a gene, a centromere, and any combination thereof.

47. The FIR irradiation device of claim 46, wherein the gene is selected from the group consisting of an immunoglobulin gene, a T cell receptor gene, a p53 gene, a retinoblastoma gene, a proto-oncogene, and any combination thereof.

48. The FIR irradiation device of claim 43, wherein the component is selected from the group consisting of a cytoskeleton, a centriole, a nuclear lamin, an intermediate filament, a neurofilament, a nucleic acid, a lipid, a fatty acid, a triglyceride, a phospholipid, a steroid, a polyisoprenoid, a glycolipid, a peptide, a polypeptide, an amino acid, an amino acid-coupled transfer RNA, a nucleotide, a nucleoside, a protein, a beat-shock protein, a histone, an enzyme, a lipoprotein, a monosaccharide, a disaccharide, a polysaccharide, a lipopolysaccharide, a proteoglycan, a glycoprotein, a water molecule, a water cluster, a region of gelled vicinal water, actin, myosin, titin, troponin, tropomyosin, a microtubule, a microfilament, and any combination thereof.

49. The FIR irradiation device of claim 43, wherein the biological sample is an organism.

50. The FIR irradiation device of claim 49, wherein the organism is a microorganism.

51. The FIR irradiation device of claim 43, wherein the component comprises an organ.

52. The FIR irradiation device of claim 51, wherein the organ is selected from the group consisting of skin, a brain, a meninx, an artery, a vein, an eye, an optic nerve, a cochlea, an olfactory nerve, an oculomotor nerve, a trochlear nerve, a trigeminal nerve, an abducent nerve, a facial nerve, a vestibulocochlear nerve, a glossopharyngeal nerve, a vagus nerve, a spinal accessory nerve, a hypoglossal nerve, a brainstem, a spinal cord, a nerve root, a neuron, a bone, a muscle, a nasopharynx, an oropharynx, an esophagus, a stomach, a duodenum, a jejunum, an ileum, a colon, a rectum, an anus, a heart, an aorta, a femoral artery, a popliteal artery, a common carotid artery, an internal carotid artery, a capillary, blood, a thymus, a thyroid, a parathyroid gland, an adrenal gland, a pituitary gland, a kidney, a lung, a trachea, a brochiole, an alveolus, a pancreas, a hand, an arm, a forearm, a leg, a foot, a thigh, a ligament, a tendon, a cartilage, connective tissue, a hair follicle, a liver, a lymph node, a gallbladder, a bile duct, a lymphatic duct, a tongue, a spleen, a ureter, a urethra, a prostate, a uterus, an ovary, a testis, a fallopian tube, a reproductive organ, a bladder, and any combination thereof.

53. The FIR irradiation device of claim 42 wherein the biological sample comprises a neoplasm.

54. The FIR irradiation device of claim 40 further comprising a lens that receives the irradiation from the filter and focuses the irradiation upon at least a portion of the sample cell.

55. The FIR irradiation device of claim 40 wherein the sample cell comprises a microarray.

56. The FIR irradiation device of claim 40 wherein the sample cell comprises a target.

57. The FIR irradiation device of claim 56 wherein the target receives substantially all of the irradiation emitted from the filter.

58. The FIR irradiation device of claim 57 wherein the target has a diameter in the range of about 1 micron to about 2 meters.

59. The FIR irradiation device of claim 58 wherein the target has a diameter in the range of about 1 micron to about 1 millimeter.

60. The FIR irradiation device of claim 59 wherein the target has a diameter in the range of about 10 microns to 100 microns.

61. The FIR irradiation device of claim 59 wherein the target has a diameter in the range of about 100 microns to 1 millimeter.

62. The FIR irradiation device of claim 58 wherein the target has a diameter in the range of about 1 centimeter to about 10 centimeters.

63. The FIR irradiation device of claim 6 further comprising a detector, receiving a residual quantity of the irradiation.

64. The FIR irradiation device of claim 63 wherein a characteristic of the irradiation is determined at least in part in response to feedback from the detector.

65. The FIR irradiation device of claim 64 wherein the characteristic of the irradiation is power, irradiance, wavelength, duration, pulse rate, pulse shape, duty cycle, or bandwidth.

66. The FIR irradiation device of claim 6 wherein the source and the filter are disposed in a common housing.

67. The FIR irradiation device of claim 66 wherein the common housing comprises an output lens.

68. The FIR irradiation device of claim 67 wherein the output lens collimates the irradiation.

69. The FIR irradiation device of claim 6, wherein the filter is configured to remove substantially all X rays from the FIR irradiation.

* * * * *